(12) United States Patent
Vodyanoy et al.

(10) Patent No.: US 10,806,754 B2
(45) Date of Patent: Oct. 20, 2020

(54) ENGINEERED METAL NANOPARTICLES AND METHODS THEREOF

(71) Applicant: AUBURN UNIVERSITY, Auburn, AL (US)

(72) Inventors: Vitaly Vodyanoy, Auburn, AL (US);
Oleg Pustovyy, Auburn, AL (US);
Ludmila Globa, Auburn, AL (US);
Mahmoud Mansour, Auburn, AL (US);
Iryna Sorokulova, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 15/927,616

(22) Filed: Mar. 21, 2018

(65) Prior Publication Data
US 2018/0271904 A1  Sep. 27, 2018

Related U.S. Application Data

(60) Provisional application No. 62/474,140, filed on Mar. 21, 2017, provisional application No. 62/501,348, filed on May 4, 2017.

(51) Int. Cl.
| | | |
|---|---|---|
| *A61K 33/34* | (2006.01) |
| *A61K 33/30* | (2006.01) |
| *A61K 9/50* | (2006.01) |
| *A61P 35/00* | (2006.01) |
| *A61K 9/00* | (2006.01) |
| *A61K 47/60* | (2017.01) |
| *A61K 9/14* | (2006.01) |
| *B82Y 5/00* | (2011.01) |

(52) U.S. Cl.
CPC ............ *A61K 33/34* (2013.01); *A61K 9/0019* (2013.01); *A61K 9/14* (2013.01); *A61K 9/5031* (2013.01); *A61K 33/30* (2013.01); *A61K 47/60* (2017.08); *A61P 35/00* (2018.01); *B82Y 5/00* (2013.01); *Y10S 977/773* (2013.01); *Y10S 977/81* (2013.01); *Y10S 977/915* (2013.01)

(58) Field of Classification Search
CPC ....... A61P 35/00; A61K 33/34; A61K 9/5031; A61K 47/60; A61K 9/14; A61K 9/0019
See application file for complete search history.

(56) References Cited

U.S. PATENT DOCUMENTS

| | | | |
|---|---|---|---|
| 7,138,255 B2 | 11/2006 | Vodyanoy et al. | |
| 7,348,029 B2 | 3/2008 | Kliss et al. | |
| 7,871,772 B2 | 1/2011 | Vodyanoy et al. | |
| 7,872,108 B2 | 1/2011 | Vodyanoy et al. | |
| 8,298,793 B2 | 10/2012 | Vodyanoy et al. | |
| 8,361,505 B1 * | 1/2013 | Perry | B01J 13/0086 424/489 |
| 9,125,835 B2 * | 9/2015 | Sinko | A61K 9/5146 |
| 2007/0212331 A1 | 9/2007 | Baldassare et al. | |
| 2015/0366995 A1 | 12/2015 | Wiesner et al. | |

FOREIGN PATENT DOCUMENTS

| | | |
|---|---|---|
| JP | 2014-240512 | 12/2014 |
| WO | 2011/022350 | 2/2011 |

OTHER PUBLICATIONS

Bae et al., "Cytotoxic Effect of Zinc-Citrate Compound on Choriocarcinoma Cell Lines," Placenta, 2007, 2891), 22-30.
Bastow et al., "zinc is a potential therapeutic for chemiresistant ovarian cancer," Journal of Experimental Therapeutics & Oncology, 2011, 9(3), 175-181.
Berridge et al. "Tetrazollium dyes as tools in cell biology: new insights nto their cellular reduction," Biotechnology Annual Review, 2005,d 11, 127-152.
Bisht et al., "ZnO Nanoparticles: A Promising Anticancer Agent," Science, Technology, and Medicine, ISSN 1846-5435.
Brookes et al., "The Swipe Card Model of Odorant Recognition," Sensors, 2012, 12 (11), 15709-15749.
Butterworth et al., "Preparation of ultrafine silica- and PEG-coated magnetite particles," Colloids and surfaces A: Physiochemical and Engineering Aspects 2001, 179 (1), 93-102.
Chen et al., "Controlled growth of zinc nanowires," Materials Letters 2007, 61(1), 144-147.
Connors, K.A., "Binding constants. The Measurements of molecular complex stability," New York: John Wiley Sons, 1987. Book reference; available upon request.
Cope, J.O., "Kinetics of the oxidation of molten zinc," Transactions of the Faraday Society, 1961, 57(0), 493-503.
Deroubaix et al., X-Ray Photoelectron-Spectroscopy Analsys of Copper and Zinc-Oxides and Sulfides, Surface and Interface Analysis, 1992, 18 (1), 39-46.
Doneux et al., "Controlled Tuningnof the Ferri/Ferrocyanide Electron Transfer at Oligo (Ethylene Glycol)-Modified Electrodes," Electrochimica Acta, 2016, 2119, 412-417.
Doneux et al., "Electron Transfer Across an Antifouling Mercaptohepta(ethylene glycol) Self-Assembled Monolayer," Journal of Physical Chemistry, C, 2016, 120 (29), 15915-15922.
Duan et al., "Effect of side chain length on the charge transport, morphology, and photovoltaic performance of conjugated polymers in bulk heterojunction solar cells," Journal of Materials Chemistry A, 2016, 4(5), 1855-1866.
Feng et al., "Flower-like PEGylated MoS2 nanoflakes for near-infrared photothermal cancer therapy," Sci Rep, 2015, 5, 17422.
Ferro et al., "Chemical surface characterization of electrochemically and thermally oxidized boron-doped diamond film electrodes, "Carbon 2005, 43(6), 1191-1203.
Fukutani et al., "An improved bioluminescence -based signaling assay for odor sensing with a yeast expressing a chimeric olfactory receptor," Biotechnol. Bioeng. 2012, 109(12), 3143-3151.
Ghosh et al., "Synergistic Anticancer Activity of Fluorescent Copper Nanoclusters and Cislatin Delivered through a Hydrogel Nanocarrier," ACS Applied materials & Interfaces, 2015, 7(1), 209-222.
Gomes et al., Ethylene Glycol: Human health aspects (Concise International Chemical Assessment Document), World Health Organization: Ottawa, Canada, 2003, p. 42.
Griffiths, D.J., Introduction to Quantum Mechanics, Prentice Hall: Upper Saddle River, New Jersey, 1995, p. 394.

(Continued)

*Primary Examiner* — Mina Haghighatian
(74) *Attorney, Agent, or Firm* — Barnes & Thornburg LLP

(57) ABSTRACT

A pharmaceutical composition comprises a metal nanoparticle having an average diameter of about 0.5 nm to about 5 nm. The composition may be used to treat cancer or an anosmia-related disease.

9 Claims, 12 Drawing Sheets

(56) References Cited

OTHER PUBLICATIONS

Gu et al., "PTCLab: free and open-source software for calculating phase transformation crystallography" Journal of Applied Crystallography, 2016, 49, 1-8.
Guay-Bégin et al., "Surface Modification of Gadolinium Oxide Thin Films and Nanoparticles using Poly(ethylene glycol)-Phosphate," Langmuir 2012, 28 (1), 774-782.
Hagerty et al.,, "After oxidation zinc nanoparticles lose their ability to enhance response to odorants," Biometals 2016, 29 (6), 1005-1018.
Hashemi et al., "Cytotoxic effects of intra and extracellular zinc chelation on human breast cancer cells," European Journal of Pharmacology, 2007, 557(1), 9-19.
Watanabe et al., "the Activation Energy for Oxygen Desorption from Zinc Oxide Surfaces," Japanese Journal of Applied Physics, 1965, 4 (12), 945.
Hotchen et al., "Amplified electron transfer at poly-ethylene-glycol (PEG) grafted electrodes," Physical Chemistry Chemical Physics, 2015, 17 (17), 11260-11268.
Jachimska et al., "Characterization of Globular Protein Solutions by Dynamic Light Scattering, Electrophoretic Mobility, and Viscosity Measurements," Langmuir, 2008, 24, 6866-6872.
Jia et al., "Enhancement of Odor-Induced Activity in the Canine Brain by Zinc Nanoparticles: A Functional MRI Study in Fully Unrestrained Conscious Dogs," Chem Senses 2016, 41 91), 53-67.
Jokerst et al., "Nanoparticle PEGylation for imaging and therapy," Nanomedicine (London, England) 2011, 6(4), 715-728.
Jose et al., "Singlet oxygen mediated DNA degradation by copper nanoparticles: potential towards cytotoxic effect on cancer cells," Journal of Nanobiotechnology, 2011, 9:9.
Kabra et al., "Dynamics of polymer matrix in non-polar solvent using TDR technique," Bionano Frontier, vol. 8 (3) Dec. 2015, 373-380.
Karakoti et al., "PEGylated Inorganic Nanoparticles," Angewandte Chemie International Ediction 2011, 50(9), 1980-1994.
Knecht et al., "Recording of the human electro-olfactogram," Physiol Behav 2004, 83 (1), 13-9.
Kohane, D.S., "Microparticles and nanoparticles for drug delivery," Biotechnol Bioeng. 2007, 96(2), 203-209.
Kriedt et al., "Zinc functions as a cytotoxic agent for prostate cancer cells independent of culture and growth conditions," J Exp Ther Oncol., 2010, 8(4), 287-295.
Kruyt, H.R. "Colloid Science," vol. VI, New York, Eslsevier, 1952. Book reference; available upon request.
Kuchel et al., "Theory and Problems of Bio-chemistry," New York, McGraw-Hill, 1988. Book reference; available upon request.
Lu et al., "One-dimensional Growth of Zinc Crystals on a Liquid surface," Sci Rep 2016, 6, 19870.
Mai et al., "Chemical synthesis of blue-emitting metallic zinc nano-hexagons," Cryst Eng Comm 2013, 15 (33), 6606-6610.
Mason, M., "Electronic structure of supported small metal clusters," Physical Review B, 1983, 27(2), 748-762.
Mathew et al., "Folate conjugated carboxymethyl chitosan-manganese doped zinc sulphide nanoparticles for targeted drug delivery and imaging o cancer cells," Carbohydrate Polymers, 2010, 80(2), 442-448.
Moore et al., "Kinetics of the formation of oxide films on the zinc foil," Transactiosn of the Faraday Society, 1951, 47(0), 501-508.
Moore et al., "Olfactory response to explosives associated odorants are enhanced by zinc nanoparticles," Talanta 2012, 88, 730-733.
Mu et al., "Chemical Basis of Interactions between Engineered Nanoparticles and Biological Systems," Chemical Reviews 2014, 114 9150, 7740-7781.
Naumkin et al., NIST X-ray Photoelectron Spectroscopy Database, NIST: Washington, 2012. Book reference available upon request.
Ndong et al., "Tumor Cell Targeting by Iron Oxide Nanoparticles in Dominated by Different Factors in Vitro versus in Vivo," PLoS One, 2015, 10(2): e0115636.

Nekoueian et al., "Interfacial Electron-Shuttling Processes across KolliphorEl Monolayer Grafted Electrodes," ACS Applied Materials & Interfaces, 2015, 7 (28), 15458-15465.
Perry et al., "PEGylated Print Nanoparticles,: The Impact of PEG Density on Protein Binding, Macrophage Association, Biodistribution, and Pharmacokinetics," Nano Letters, 2012, 12 (10), 53304-5310.
Qiu et al., "Evidence of a unique electron Donor-Acceptor Property for Platinum Nanoparticles as Studied by XPS," Langmuir, 2006, 22 (10), 4480-4482.
Samoylov et al., "Novel Metal Clusters Isolated from Blood Are Lethal to Cancer Cells," Cells Tissues Organs 2005, 179 (3), 115-124.
Sannaningannavar et al., "Activation energy ($\Delta G^*$), enthalpy ($\Delta H^*$), and entrypy ($\Delta S^*$) of poly(ethylene glycol) using Higasi method," Polymer bulletin, 2016, 73 (6), 1689-1700.
Schaeublin et al., "Surface charge of gold nanoparticles mediates mechanism of toxicity," Nanoscale, 2011:3(2), 410-420.
Schulte et al., "Effect of pressure on the atomic volune of Zn, Cd, and Hg up to 75 GPa," Physical Review B, 53(2), 569-580.
Scott et al., The electroolfactogram: A review of its history and uses, Microscopy Research and Technique, 2002, 58(3), 152-160.
Segel et al., "Biochemical Calculations," 2d ed., ed. John Wiley & Sons: New York, 1976. Book reference; available upon request.
Segel et al., "Biochemical Calculations," John Wiley & Sons: New York, 1975. Book reference; available upon request.
Shah et al., "Direct intra-tumoral injection of zinc-acetate halts tumor growth in a xenoraft model of prostate cancer," Journal of Experimental & Clinical Cancer Research, 2009, 28.
Singletary et al., "PEGylation of zinc nanoparticles amplifies their ability to enhance olfactory responses to odorant," PLoS One, Dec. 20, 2017, https://doi.org/10.1371/hournal.pone.0189273.
Smith et al., "Real-time intravital imaging of RGD-quantum dot binding to luminal endothelium in mouse tumor neovasculature," Nano Lett 2008, 8 (9), 2599-606.
Smolne et al., "Propagation and Termination Kinetics of Poly(Ethylene Glycol) Methyl Ether Methacrylate in Aqueous Solution," Macromolecular Chemistry and Physics, 2016, 217 (21), 2391-2401.
Studer et al., "Nanoparticle cytotoxicity depends on intracellular solubility: comparison of stabilized copper metal and degradable copper oxide nanoparticles," Toxicol Lett. 2010, 197(3): 169-174.
Thierry et al., "A Robust procedure for the functionalization of gold nanorods and noble metal nanoparticles," Chemical Communications, 2009, (13), 1724-1726.
Tokushige et al., "Plasma-induced cathodic discharge electrolysis to form various metal/alloy nanoparticles," Russian Journal of Electrochemistry, 2010, 46(6), 619-626.
Turin, L., "A spectroscopic mechanism for primary olfactory reception," Chem Senses 1996, 21(6), 773-791.
Uzzo et al., "Zinc inhibits nuclear factor-kappa B activation and sensitizes prostate cancer cells to cytotoxic agents," Clinical Cancer Research: an official journal of the American Association for Cancer Research, 2002, 8(11), 3579-3583.
Vainrub et al., "Resolution of 90 nm (lambda/5) in an optical transmission microscope with an annular condenser," Opt. Lett. 2006, 31 (19), 2855-2857.
Viswaprakash et al., "Enhancement of Odorant-Induced Response in Olfactory Receptor Neurons by Zinc Nanoparticles," Chem. Senses, 2009, 34, 547-557.
Vodyanoy et al., "Engineered metal nanoparticles in the sub-nanomolar levels kill cancer cells," Int. J. Nanomedicine, 2016, 11: 1567-1576.
Vodyanoy, V., "Zinc nanoparticles interact with olfactory receptor neurons," Biometals 1020, 23 (6), 1097-1103.
Wang et al, "Biocompatible PEGylated MoS2 nanosheets: Controllable bottom-up synthesis and Highly efficient photothermal regression of tumor," biomaterials, 2015, 39, 206-217.
Wang et al., "Synthesis and characterization of green agents coated Pd/Fe bimetallic nanoparticles," Journal of the Taiwan Institute of Chemical Engineers, 2015, 50, 297305.

(56) References Cited

OTHER PUBLICATIONS

Wang et la., "Molecular Weight Dependence of Viscosity and Shear Modulus of Polyethylene Glycol (PEG) Solution Boundary Layers," The Journal of Physical Chemistry C, 2009, 113 (31), 13793-13800.

Xue et al., "Staurosporine-induced death of MCG-7 human breast cancer cells: A distinction between caspase-3-dependent steps of apoptosis and the critical lethal lesions," Exp Cell Res 2003, 283:135-145.

* cited by examiner

ENGINEERED METAL NANOPARTICLES AND METHODS THEREOF

CROSS-REFERENCE TO RELATED APPLICATIONS

This application claims priority under 35 U.S.C. § 119(e) to U.S. Provisional Application Nos. 62/501,348, filed May 4, 2017, and 62/474,140, filed Mar. 21, 2017, which are expressly incorporated by reference herein.

GOVERNMENT LICENSE RIGHTS

This invention was made with government support under 70NANB14H324 awarded by the National Institute of Standards and Technology. The government has certain rights in the invention.

TECHNICAL FIELD

The invention relates to engineered metal nanoparticles for treating diseases. The invention includes compositions and methods related to engineered metal nanoparticles, including methods and compositions for treating cancer and anosmia-related diseases.

BACKGROUND

Metal nanoparticles are present in and have been isolated from the blood of several vertebrate species. These metal nanoparticles have been obtained as part of protein nucleating centers (PNCs) isolated from animal blood.

Investigations into PNCs have revealed that these compositions may be toxic to cultured cancer cells at low concentrations, such as nanomolar concentrations. Lethal concentrations of synthetic metal nanoparticles reported in the literature are orders of magnitude higher than the natural, blood-isolated metal nanoparticles. Additionally, olfactory responses have been enhanced with the addition of endogenous zinc nanoparticles.

SUMMARY

The present disclosure describes engineered nanoparticles for use in treating diseases. The nanoparticles are effective at lower concentrations than nanoparticles that have been used in the art. Advantageously, the engineered nanoparticles are formed without the need for animal sources, such as animal blood.

The following numbered embodiments are contemplated and are non-limiting:

1. A pharmaceutical composition comprising a therapeutically effective amount of a metal nanoparticle.
2. The pharmaceutical composition of clause 1, wherein the metal nanoparticle has an average diameter of about 0.5 nm to about 5 nm.
3. The pharmaceutical composition of clause 1 or 2, wherein the metal nanoparticle has an average diameter of about 1 nm to about 3 nm.
4. The pharmaceutical composition of any of the preceding clauses, wherein the metal nanoparticle has an average diameter of about 1 nm to about 2.5 nm.
5. The pharmaceutical composition of any of the preceding clauses, wherein the metal nanoparticle has an average diameter of about 1.2 nm.
6. The pharmaceutical composition of any of the preceding clauses, wherein the metal nanoparticle has an average diameter of about 2.1 nm.
7. The pharmaceutical composition of any of the preceding clauses, wherein the metal nanoparticle comprises about 25 atoms to about 100 atoms.
8. The pharmaceutical composition of any of the preceding clauses, wherein the metal nanoparticle comprises about 30 atoms to about 60 atoms.
9. The pharmaceutical composition of any of the preceding clauses, further comprising an excipient.
10. The pharmaceutical composition of any of the preceding clauses, wherein the metal nanoparticle comprises a metal selected from the group consisting of copper, iron, zinc, silver, gold, platinum, and magnesium.
11. The pharmaceutical composition of any of the preceding clauses, wherein less than about 50% of the metal nanoparticle is oxidized.
12. The pharmaceutical composition of any of the preceding clauses, wherein less than about 15% of the metal nanoparticle is oxidized.
13. The pharmaceutical composition of any of the preceding clauses, wherein less than about 5% of the metal nanoparticle is oxidized.
14. The pharmaceutical composition of any of the preceding clauses, wherein the metal nanoparticle has a purity of at least 95 wt. %.
15. The pharmaceutical composition of any of the preceding clauses, wherein the metal nanoparticle has a purity of at least 99 wt. %.
16. The pharmaceutical composition of any of the preceding clauses, wherein the metal nanoparticle is formed by an underwater high-voltage discharge method.
17. The pharmaceutical composition of clause 16, wherein the underwater high-voltage discharge method comprises applying a voltage of about 10,000 volts to about 20,000 volts to metal electrodes and creating an electric discharge.
18. The pharmaceutical composition of clause 16 or 17, wherein the underwater high-voltage discharge method comprises applying a voltage of about 15,000 volts and creating an electric discharge.
19. The pharmaceutical composition of clause 17 or 18, wherein the metal nanoparticle isolated by centrifugation.
20. The pharmaceutical composition of any of the preceding clauses, wherein the metal nanoparticle further comprises a coating.
21. The pharmaceutical composition of clause 20, wherein the coating surrounds the periphery of the metal nanoparticle.
22. The pharmaceutical composition of clause 20 or 21, wherein the coating comprises a polypeptide or a polyether.
23. The pharmaceutical composition of any of clauses 20 to 22, wherein the coating comprises polyethylene glycol.
24. The pharmaceutical composition of clause 23, wherein the polyethylene glycol has a molecular weight of about 200 g/mol to about 1000 g/mol.
25. The pharmaceutical composition of clause 23 to 24, wherein the polyethylene glycol has a molecular weight of about 400 g/mol.
26. The pharmaceutical composition of any one of clauses 20 to 25, wherein coating is covalently bonded to the metal nanoparticle.
27. The pharmaceutical composition of any one of clauses 20 to 26, wherein the coating withdraws electron charge from the metal nanoparticle and increases binding energy to the metal nanoparticle.

28. The pharmaceutical composition of any one of clauses 20 to 26, wherein the coating donates electron charge to the metal nanoparticle and decreases binding energy to the metal nanoparticle.

29. The pharmaceutical composition of any one of clauses 20 to 28, wherein the coating and the metal nanoparticle form a conjugated electron system.

30. A method of treating cancer in a patient, comprising administering to the patient a therapeutically effective amount of a metal nanoparticle of any one of the preceding clauses.

31. The method of clause 30, wherein the viability of a cancerous cell line decreases by at least about 75%.

32. The method of clause 30 or 31, wherein the viability of a cancerous cell line decreases by at least about 90%.

33. The method of clause 31 or 32, wherein the viability of the cancerous cell line is reduced in a dose-dependent manner.

34. The method of any of clauses 30 to 33, wherein the metal nanoparticle selectively causes apoptosis in cancerous cells compared to noncancerous cells.

35. The method of clause 34, wherein the noncancerous cells are noncancerous astrocytes.

36. The method of clause 35, wherein at least about 50% of the noncancerous astrocytes remain viable.

37. The method of clause 35 or 36, wherein at least about 75% of the noncancerous astrocytes remain viable.

38. The method of any of clauses 30 to 37, wherein cell adherence is decreased.

39. The method of any of clauses 30 to 38, wherein cell shrinking occurs.

40. The method of any of clauses 30 to 39, wherein cell rounding occurs.

41. The method of any of clauses 30 to 40, wherein nuclear condensation occurs.

42. The method of any of clauses 30 to 41, wherein the cancer is brain cancer or prostate cancer.

43. The method of any of clauses 30 to 42, wherein the cancer comprises a cancerous cell line selected from the group consisting of Hs683 cells, SVGp12 cells, PC3 cells, U937 cells, and HeLa cells.

44. The method of any of clauses 30 to 43, wherein the metal nanoparticle is applied at a dose of about 0.01 nM to about 1.0 nM.

45. The method of any of clauses 30 to 44, wherein the metal nanoparticle is applied at a dose of about 0.05 nM to about 0.3 nM.

45. The method of any of clauses 30 to 44, wherein the metal nanoparticle is applied at a dose of about 0.01 nM to about 0.1 nM.

46. A method of treating an anosmia-related disease in a patient, comprising administering to the patient a therapeutically effective amount of a metal nanoparticle of any one of the preceding clauses.

47. The method of clause 46, wherein the anosmia-related disease is Alzheimer's disease.

48. The method of clause 46, wherein the anosmia-related disease is Parkinson's disease.

49. The method of any one of clauses 46 to 48, wherein olfactory response is enhanced for about 10 days.

50. The method of any one of clauses 46 to 49, wherein olfactory response is enhanced for about 100 days.

51. The method of any one of clauses 46 to 50, wherein olfactory response is enhanced for about 300 days.

52. The method of any of clauses 46 to 51, wherein the metal nanoparticle is applied at a dose of about 0.01 nM to about 1.0 nM.

53. The method of any of clauses 46 to 52, wherein the metal nanoparticle is applied at a dose of about 0.05 nM to about 0.3 nM.

54. The method of any of clauses 46 to 52, wherein the metal nanoparticle is applied at a dose of about 0.01 nM to about 0.1 nM.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which.

DETAILED DESCRIPTION

Figures 1A, 1B, 1C, 1D, 1E, 1F:
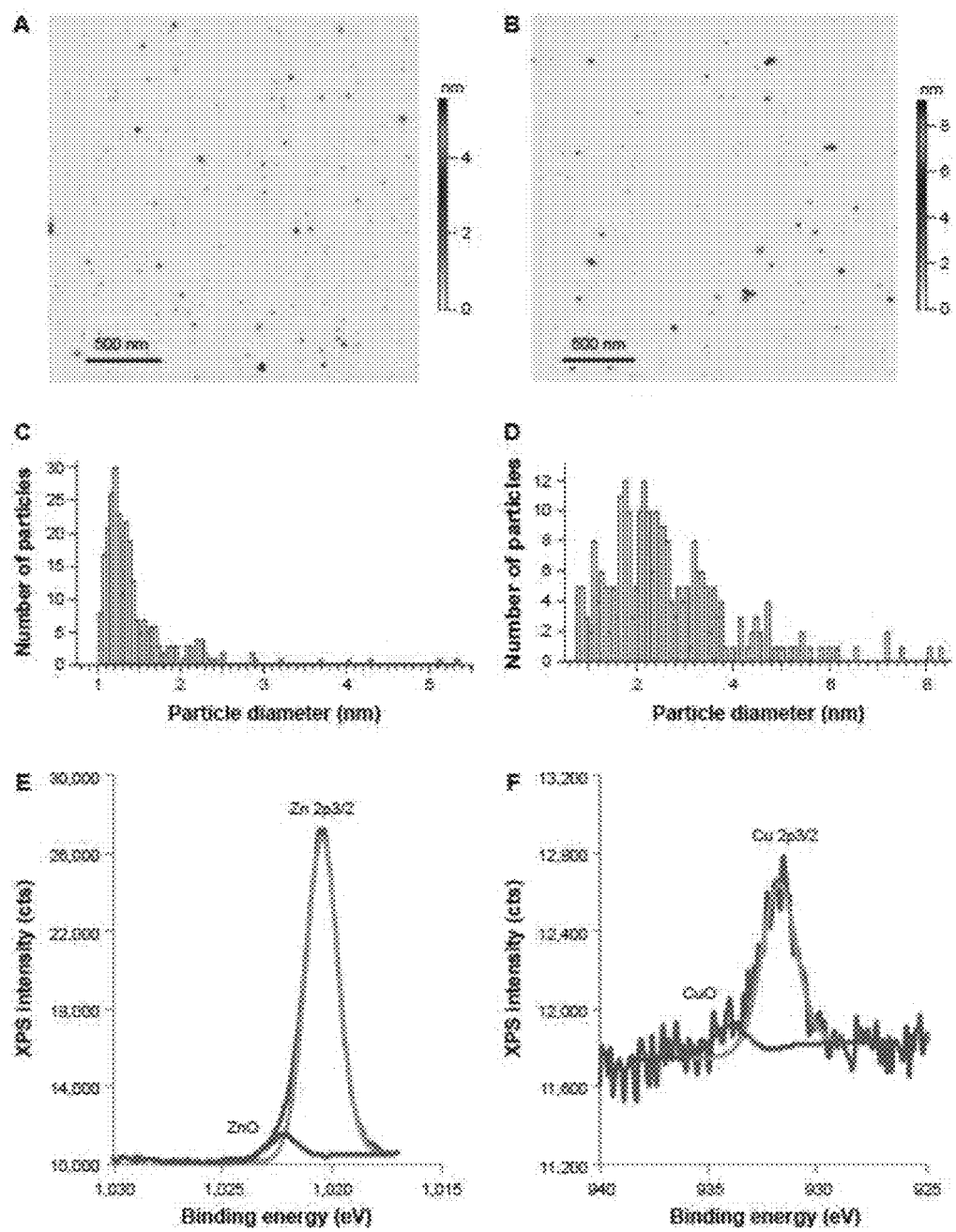
FIG. 1A shows an atomic force microscope (AFM) image of 0.01% zinc nanoparticles on mica.
FIG. 1B shows an AFM image of 0.01% copper nanoparticles on mica.
FIG. 1C shows a size distribution of the zinc nanoparticles of FIG. 1A.
FIG. 1D shows a size distribution of the copper nanoparticles of FIG. 1B.
FIG. 1E shows an X-ray photoelectron spectroscopy (XPS) spectrum of the zinc nanoparticles of FIG. 1A.
FIG. 1F shows an XPS spectrum of the copper nanoparticles of FIG. 1B.

Various embodiments of the invention are described herein as follows. In one embodiment, metal nanoparticles are provided. The metal nanoparticles are engineered rather than being obtained from biological sources. For example, the nanoparticles do not require isolation or purification from animal sources. In some embodiments, the nanoparticles described herein may be obtained at lower costs than those obtained from biological sources.

Additionally, the metal nanoparticles of the present disclosure are effective at low concentrations, such as nanomolar and subnanomolar concentrations. Furthermore, the nanoparticles described herein may mimic properties of endogenous metal nanoparticles and may cause limited side effects compared to other therapeutics.

In some embodiments, the metal nanoparticles of the present disclosure comprise or consist essentially of a plurality of non-oxidized metal atoms. The metal atoms may be selected from the group consisting of zinc, copper, iron, gold, silver, platinum, and magnesium. In some embodiments, the nanoparticles comprise or consist essentially of only one type of atom rather than a mixture of atoms.

In some embodiments, the metal nanoparticles are of high purity and free from contamination. As used herein, purity refers to the amount of the particle's constituent metal atoms compared to all atoms. The purity, as determined based on weight, of the metal nanoparticles may be at least about 50%, at least about 75%, at least about 85%, at least about 90%, at least about 95%, at least about 99%, from about 50% to about 99.9%, from about 75% to about 99.9%, from about 85% to about 99.9%, from about 90% to about 99.9%, from about 95% to about 99.9%, or from about 99% to about 99.9%.

In some embodiments, the nanoparticles are primarily in a nonoxidized, elemental state rather than being oxidized. In some embodiments, the percentage of metal nanoparticles, based on molar ratio, that are nonoxidized is least about 50%, at least about 75%, at least about 85%, at least about 90%, at least about 95%, or at least about 99%. In some embodiments purity of the nanoparticles and/or the amount of oxidation in the particles is determined by XPS.

In some embodiments, the metal nanoparticles are in crystalline form. The crystal structure of the metal nanoparticles is the same or substantially the same as the most stable bulk crystal structure of the nanoparticle's constituent atoms.

In some embodiments, the nanoparticles are a plurality of small particles. Without intending to be bound by theory, this small size might facilitate with cellular uptake or excretion. For example, it is believed that small, uncharged nanoparticles of can efficiently penetrate through the external and nuclear membranes and create aggregates. The average diameter of the particles may be less than about 50 nm, less than about 40 nm, less than about 30 nm, less than about 20 nm, less than about 10 nm, less than about 5 nm, less than about 4 nm, less than about 3 nm, less than about 2 nm, from about 0.5 nm to about 50 nm, from about 0.5 nm to about 40 nm, from about 0.5 nm to about 30 nm, from about 0.5 nm to about 20 nm, from about 0.5 nm to about 10 nm, from about 0.5 nm to about 5 nm, from about 0.5 nm to about 4 nm, from about 0.5 nm to about 3 nm, from about 0.5 nm to about 2 nm, from about 1 nm to about 50 nm, from about 1 nm to about 40 nm, from about 1 nm to about 30 nm, from about 1 nm to about 20 nm, from about 1 nm to about 10 nm, from about 1 nm to about 5 nm, from about 1 nm to about 4 nm, from about 1 nm to about 3 nm, from about 1 nm to about 2 nm, about 1 nm, or about 2 nm.

In some embodiments, the nanoparticles of the present disclosure are made of fewer than about 300 atoms, fewer than about 200 atoms, fewer than about 100 atoms, fewer than about 75 atoms, fewer than about 65 atoms, fewer than about 50 atoms, about 10 to about 100 atoms, about 10 to about 75 atoms, about 10 to about 65 atoms, about 10 to about 50 atoms, about 25 to about 300 atoms, about 25 to about 200 atoms, about 25 to about 100 atoms, about 25 to about 75 atoms, about 25 to about 65 atoms, about 25 to about 50 atoms, about 40 to about 100 atoms, about 40 to about 75 atoms, about 40 to about 65 atoms, about 40 to about 50 atoms, about 40 to about 200 atoms, about 40 to about 300 atoms, about 100 to about 200 atoms, about 100 to about 300 atoms, about 200 to about 300 atoms, or about 60 atoms.

In some embodiments, zinc nanoparticles may be engineered using a high-voltage electrical discharge method. The high-voltage electrical discharge method comprises applying an electrical potential to two bulk metal rods that are submerged in water. The bulk metal rods produce a discharge that produces metal nanoparticles.

In some embodiments, the metal rods used in the electrical discharge method are of high purity. The purity of the metal may be greater than about 99%, greater than about 99.9%, greater than about 99.99%, greater than about 99.999%, or greater than about 99.9999%. In some embodiments, the metal rods are submerged in high purity water. For example, the water may be LC-MS grade water.

The distance between the electrodes may be controlled to create a fine dispersion of metal nanoparticles. In some embodiments, the distance between the electrodes is about 0.25 cm to about 2 cm, about 0.25 cm to about 1 cm, about 0.25 to about 0.5 cm, about 0.5 cm to about 2 cm, about 0.5 cm to about 1 cm, or about 0.5 cm.

The potential applied to the electrodes may be controlled to create a fine dispersion of metal nanoparticles. In some embodiments, the voltage is an AC voltage. In some embodiments, the voltage is about 1,000 volts to about 50,000 volts, about 5,000 volts to about 50,000 volts, about 10,000 volts to about 50,000 volts, about 15,000 volts to about 50,000 volts, 1,000 volts to about 25,000 volts, about 5,000 volts to about 25,000 volts, about 10,000 volts to about 25,000 volts, or about 15,000 volts to about 25,000 volts. In some embodiments, the potential is sustained for at least about 1 hour.

After the voltage is applied, the suspension of nanoparticles may be allowed to rest such that large particles sediment and smaller particles remain in suspension. The suspended particles may be separated from the sediment and subjected to centrifugation. The speed and time of centrifugation, along with the number of centrifugations, may be configured to separate nanoparticles of a desired size.

In some embodiments, the metal nanoparticles described herein may be coated with one or more coating materials. The coating material may be selected from the group consisting of thiols such as thioctic acid or cysteine, phosphonic acids such as 6-phosphonohexanoic acid or neridronate, silanes such as (3-aminopropyl)triethoxysilane, peptides such as short peptides having 2 to 10 amino acids, and ethers such as polyethylene glycol or polypropylene glycol. In some embodiments, the coating is covalently bonded to the metal nanoparticle.

In some embodiments, the coating material is polyethylene glycol (PEG). The PEG coating may be provided by PEGylation. As used herein, PEGylation refers to a chemical process comprising contacting the surface of a nanoparticle with PEG. The molecular weight of the PEG coating may be about 100 g/mol to about 1000 g/mol, about 200 g/mol to about 1000 g/mol, about 300 g/mol to about 1000 g/mol, about 400 g/mol to about 1000 g/mol, about 100 g/mol to about 750 g/mol, about 200 g/mol to about 750 g/mol, about 300 g/mol to about 750 g/mol, about 400 g/mol to about 750 g/mol, about 100 g/mol to about 500 g/mol, about 200 g/mol to about 500 g/mol, about 300 g/mol to about 500 g/mol, or about 400 g/mol to about 500 g/mol.

In some embodiments, the coating material may improve the stability and avoid degradation of the metal nanoparticle. For example, the coating material may allow the metal nanoparticle to remain in the elemental state, i.e., not be oxidized, for a longer period of time than an uncoated nanoparticle. Additionally, the coating material may be configured to improve the binding properties of the metal nanoparticle. The protection of metal nanoparticles from rapid oxidation and improvement of their biophysical and biochemical properties may provide for better interactions with receptors, compatibility of the particle-cell interface, and/or reduced toxicity. In some embodiments, the coating may offer antibacterial activity.

Without intending to be bound by theory, in some embodiments, the coating may interact with the atoms of the metal nanoparticles in such a way that the electronic structure of the nanoparticles is affected, and a conjugated electron system is produced. For example, the coating may withdraw electron charge and increase the binding energy to the particle. Conversely, the coating may act as a passivation layer that leads to a reduction in binding energy because of the fact that the zinc nanoparticles are acting as electron donors. It is contemplated that the length, viscosity, and/or rigidity of the coating may be adjusted, such as to increase electron transmission probability.

For example, in some embodiments, PEGylation may decrease the rate of oxidation of the nanoparticles. Additionally, PEGylation may provide an increased affinity to a target protein and reduced cytotoxicity of nanoparticles relative to nanoparticles that are not PEGylated.

In some embodiments, the metal nanoparticles described herein specifically interact with proteins, peptides, and/or nucleic acids. In some embodiments, the metal nanoparticles are part of nanoparticle-based drugs, which may cross biological barriers.

It is contemplated that the metal nanoparticles are part of a pharmaceutical composition. As used herein "pharmaceutical composition" or "composition" refers to a mixture of one or more of the metal nanoparticles described herein, which may comprise other chemical components, such as pharmaceutically acceptable excipients. The purpose of a pharmaceutical composition is to facilitate administration of a metal nanoparticle to a subject. Pharmaceutical compositions suitable for the delivery of metal nanoparticles described and methods for their preparation will be readily apparent to those skilled in the art. A "pharmaceutically acceptable excipient" refers to an inert substance added to a pharmaceutical composition to further facilitate administration of a conjugate such as a diluent or a carrier. In some embodiments, the pharmaceutical composition comprises metal nanoparticles in a solution without other chemical components.

In some embodiments, the nanoparticles are effective in treating the diseases described herein in a dose-dependent manner at nanomolar or sub-nanomolar concentrations. The metal nanoparticles and pharmaceutical compositions thereof may be used at a dose of about 0.01 nM to about 1.0 nM, about 0.01 nM to about 0.5 nM, about 0.01 nM to about 0.3 nM, about 0.01 nM to about 0.1 nM, about 0.05 nM to about 1.0 nM, about 0.05 nM to about 0.5 nM, about 0.05 nM to about 0.3 nM, or about 0.05 nM to about 0.1 nM.

In some embodiments, the metal nanoparticles and pharmaceutical compositions are administered to a patient to treat cancer. In preferred embodiments, the metal nanoparticle used to treat cancer is made of platinum, gold, zinc, copper, iron, or silver.

It is contemplated that the nanoparticles described herein may be administered to treat cancer selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, metastatic breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, cancer of the urethra, cancer of the penis, prostate cancer, chronic leukemia, acute leukemia, lymphocytic lymphomas, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, glioma, brain stem glioma, pituitary adenoma, and adenocarcinoma of the gastroesophageal junction. In some aspects of these embodiments, the cancer is a primary or secondary brain cancer.

In some embodiments, the cancer comprises a cancerous cell line selected from the group consisting of Hs683 cells, SVGp12 cells, PC3 cells, U937 cells, and HeLa cells.

In some embodiments, the metal nanoparticle selectively causes apoptosis in cancerous cells compared to noncancerous cells. In some embodiments, after incubation with a metal nanoparticle of the present disclosure, the viability of a cell line may decrease in a dose-dependent manner. The viability of a cell line may decrease by at least about 50%, at least about 60%, at least about 70%, at least about 80%, at least about 90%, or at least about 95%. In some embodiments, the viability of noncancerous cells may be reduced by less than about 50%, less than about 40%, less than about 30%, less than about 20%, or less than about 10%.

In some embodiments, exposure to the nanoparticles results in cell morphological changes, including but not limited to decreased cell adherence, shrinking/rounding, nuclear condensation, and budding from cell bodies. The metal-induced cell injuries may be similar to the effects of staurosporine, an active apoptotic reagent.

Without intending to be bound by theory, it is believed that metal nanoparticles may aggregate inside cancer cells. Large aggregates may be recognized as foreign particles and expelled by exocytosis. It is believed that when many aggregate particles leave the cell, the external cell membrane may deplete causing nucleus budding and cell death.

It is contemplated that the nanoparticles described herein may be administered to treat an anosmia-related disease in a patient. In preferred embodiments, the metal nanoparticle used to treat the anosmia-related disease is made of zinc. The metal nanoparticles of the present disclosure demonstrated a significant enhancement of olfactory responses to odorant stimulation. In some embodiments, the olfactory response is enhanced for about 10 days, about 50 days, about 100 days, about 150 days, about 200 days, about 250 days, or about 300 days.

Without intending to be bound by theory, it is believed that, when nanoparticles are coated, the coating may increase binding affinity to olfactory receptors in part due to a reduction of the surface charge and/or because of an increase of hydrophobicity. The nanoparticles may increase the concentration of receptor dimers and may serve as electron donors for tunnel electron transport. Additionally, while oxidation of metal nanoparticles may eliminate the observed enhancement of olfactory responses, the coatings described herein may limit oxidization such that the enhancement is retained.

In some embodiments, the engineered zinc nanoparticles added to an odorant cause a significant rise of olfactory associated brain activity. In some embodiments, the metal nanoparticles and compositions thereof are administered to a patient suffering from Alzheimer's disease or Parkinson's disease.

EXAMPLES

Optical Microscopy

An illumination optical system with a high-aperture cardioid annular condenser was used in this work. The system produces a highly oblique hollow cone of light (numerical aperture [NA]=1.2-1.4). The illumination system was positioned in an Olympus BX51 microscope by replacing a regular condenser. The illumination system was connected with a light source (EXFO120; Photonic Solution Ltd, Edinburgh, UK) by a liquid light guide. The objective used for this work was an infinity-corrected objective HCX PL APO 100/1.40-0.70, oil, iris from Leica. The image was magnified by a zoom intermediate lens (2×-U-CA, Olympus Corporation, Shinjuku, Tokyo City, Tokyo, Japan), a home-built 40× relay lens, and captured by a Sony MCC-500MD video and a Dimension 8200 Dell computer. The microscope was placed on a vibration-isolated platform (manufactured by TMC, Peabody, Mass., USA).

Atomic Force Microscopic

Images of metal nanoparticles were taken by Bruker MultiMode 8 (Santa Barbara, Calif., USA) atomic force microscope in Tapping® (intermittent-contact) mode, using PointProbe® Plus SEIKO microscopes—Non-Contact/Tapping Mode High Force Constant (PPP-SEIH) made by Nanosensors™ (Neuchatel, Switzerland) AFM probes. The nominal values specified by the vendor for the force constant and resonance frequency of these probes were 15 N/m and 130 kHz, respectively.

Monolayers of nanoparticles were prepared on a mica substrate for all measurements by adding small amount of 0.01% nanoparticles solution on freshly cleaved mica surfaces. AFM imaging was used to measure the size distribution of particles. Size distributions of nanoparticles were measured in five independent scans over different areas.

X-Ray Photoelectron Spectroscopy

The Kratos Axis Ultra delay-line detector instrument in hybrid mode using a monochromatic Al Kα1,2 X-ray source (hv=1,486.6 eV) was used for X-ray photoelectron spectroscopy (XPS). High-resolution spectra of Zn 2p (1,017-1,057 eV) and Cu 2p (925-965 eV) were acquired using a pass energy of 40 eV with an energy resolution of 0.1 eV.

Nanoparticles were analyzed in a water suspension on gold-coated silicon wafers and evaporated during evacuation of the system. XPS was used to make quantitative spectroscopic measurements of the elemental composition of the nanoparticles' surfaces.

Zeta Potential

Zeta potentials of the nanoparticles in water suspension were determined with a Zetasizer Nano ZSP (Malvern Instruments, Worcestershire, UK) using the laser Doppler velocimetry technique. The results of six sequential runs were averaged.

Zeta potentials were calculated with Henry's equation:

$$\zeta = 3\eta\mu/2\varepsilon F(k\alpha)$$

in which $\zeta$ is the zeta potential, $\eta$ is the viscosity, $\mu$ is the electrophoretic mobility, $\varepsilon$ is the dielectric constant of the medium and $F(k\alpha)$ is Henry's function, which equals 1.5 using the Smoluchowski approximation.

Transmission Electron Microscopy

Transmission electron microscopy (TEM) was carried out utilizing an FEI Titan operated at 80 kV and 300 kV. Small drops of nanoparticle water suspension were deposited onto a QUANTIFOIL® Holey Carbon Film on copper TEM grids. Widths of the interference fringes were measured and the Miller-Bravais indices of the crystalline structures were estimated by the Crystallography lab software.

Example 1

Preparation of Metal Nanoparticles

Engineered zinc and copper nanoparticles were prepared using a high-voltage discharge method from bulk metal rods. By controlling the voltage and distance between the electrodes, the plasma created under water produced a fine dispersion of metal nanoparticles.

Specifically, two metal electrodes (99.9999%; Alfa Aesar, Haverhill, Mass., USA) of 2 mm diameter were positioned in a large Pyrex jar 1 mm below the gas-water interface. The distance between the rods was about 0.5 cm. 750 mL of double distilled water that was autoclaved (23 psi, 120° C.) (Omnisolv, Charlotte, N.C., USA) was used. The water was chilled to 25° C. and percolated with nitrogen gas for 20 min. The jar was in the water bath with running water to prevent overheating. An AC voltage of 15,000 volts was applied to electrodes and the electric discharge was sustained for 1 hour. Next, the water suspension was collected in 1 L glass beaker and placed in a refrigerator for 12 hours to allow large metal particles to sediment. Then, the suspended particles were separated from the sediment and subjected to centrifugation at 15,000×g for 2 hours at 25° C. After centrifugation, the pellet was discarded and the supernatant was subjected to further centrifugations to produce fractions of nanoparticles enriched in particles of particular sizes. The centrifuge speed and time to separate nanoparticles by size was estimated with a Stock's equation. The total concentration of metal in the suspension was measured by atomic absorption spectra (GTW Analytical Services, Memphis, Tenn., USA), and the size and the number of particles were determined by atomic force microscopy.

Example 2

Properties of Metal Nanoparticles

Atomic force microscopy revealed the size distributions of Zn and Cu nanoparticles prepared according to Example 1. As shown in FIG. 1A, a total of 270 nanoparticles with a height of above 1 nm were detected over a 2.5 $\mu m^2$ area, and Zn nanoparticles had an average diameter of 1.2±0.3 nm. As shown in FIG. 1B, 257 nanoparticles with a height of above 0.75 nm were detected over a 2.5 $\mu m^2$ area, and Cu nanoparticles had an average diameter of 2.1±0.6 nm.

FIGS. 1C and 1D show histograms for Zn and Cu nanoparticles, respectively, based on the atomic force microscopy data. The histograms represent distributions with relatively high peaks around average particle diameter values and tails up to 6 nm. Standard deviations (SDs) were calculated from the bell distributions around the peaks. The nanoparticles were homogenously distributed with polydispersity indexes of 0.062 and 0.082 for zinc and copper, respectively.

FIGS. 1E and 1F shows high-resolution XPS of Zn 2p3/2 and Cu 2p3/2, respectively. As shown in FIG. 1E, the spectra for metal and metal oxide species show 93.9%±3.4% and 5.9%±3.7% of Zn and ZnO, respectively. As shown in FIG. 1F, the spectra for metal and metal oxide species show 85.8%±4.1% and 14.2%±4.1% of Cu and CuO, respectively. These data indicate that, in both instances, more than 85% of metal atoms were not oxidized.

Zeta potentials for zinc and copper nanoparticles in water suspension were $\zeta=-15.4\pm0.8$ (SD) mV and $\zeta_{Cu}=-17.4\pm1.7$ (SD) mV.

Example 3

Cell Viability Assay

Two rat glioma cell lines (RG2 and F98) and rat astrocytes (CTX TNA2) transfected with SV40 were obtained from the American Type Culture Collection (ATCC) and maintained as recommended by ATCC.

A 3-[4,5-dimethylthiazol-2-yl]-2,5-diphenyl tetrazolium bromide (MTT) assay was used to measure the effect of metal nanoparticles on cell viability. Eight experiments with zinc nanoparticles and five experiments with copper nanoparticles and RG2 cells were performed. Sixteen control experiments with zinc and copper nanoparticles and CTX astrocytes were performed. Experiments tested cells in six conditions: untreated cells, metal nanoparticles at four different sub-nanomolar concentrations, or 1 μmol/L of staurosporine added to cells. Each condition was repeated six times. Results are presented as mean values for each condition±standard error (SE).

Cells were plated in D5648 media (Sigma 96-well polystyrene plates) at a density of 3×103 cells/well. At 24 hours after plating, the medium was replaced with Dulbecco's Modified Eagle's Medium (100 μL/well) containing 1 μmol/L staurosporine, or zinc or copper nanoparticles with various concentrations (0.05-0.3 nm). At 20 hours after treatment, a 20 μL aliquot of MTT (5 mg/mL in phosphate buffer solution [PBS]) was added to each well, and the cells were incubated for 4 hours at 37° C. MTT was reduced in metabolically active cells to form purple formazan crystals that were subsequently dissolved in dimethyl sulfoxide and quantified by a plate reader (Bio-Rad, Hercules, Calif., USA). The dye was converted to a colored product by the activity of NAD(P)H-dependent dehydrogenase enzymes, which indicated the level of energy metabolism in cells. The color development from yellow to blue was proportional to the number of metabolically active cells. The analysis was carried out with Origin: Data Analysis and Graphing Software (OriginLab).

Figures 2A, 2B, 2C, 2D:
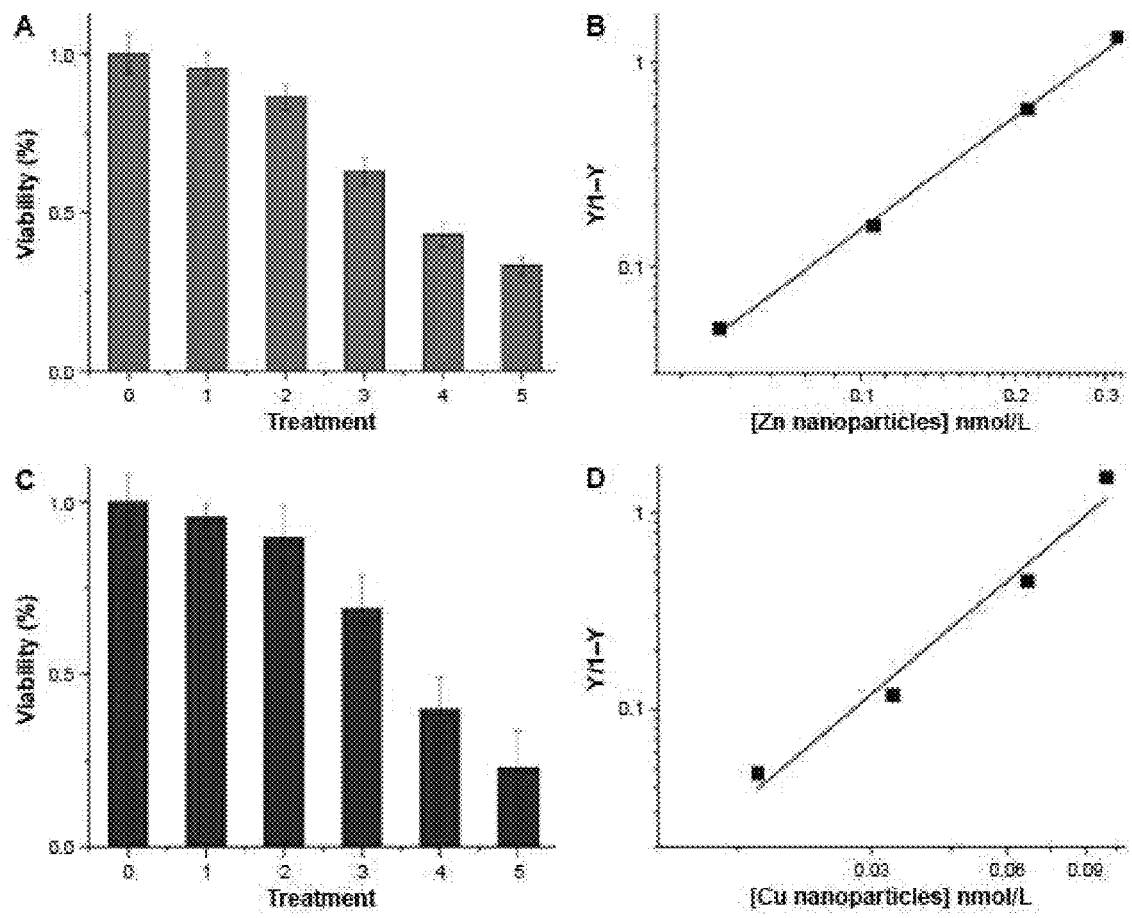
FIG. 2A shows viability of glioma cells at six experimental conditions related to treatment with zinc nanoparticles.
FIG. 2B shows a Hill presentation of glioma cell mortality based on the results shown in FIG. 2A.
FIG. 2C shows viability of glioma cells at six experimental conditions related to treatment with copper nanoparticles.
FIG. 2D shows a Hill presentation of glioma cell mortality based on the results shown in FIG. 2C.

As shown in FIG. 2A, cell death due to treatment with zinc nanoparticles was confirmed by MTT assay. The relative viability of RG2 glioma cells was reduced in a dose-dependent manner when added zinc nanoparticle concentrations increased from 0.05 nmol/L to 0.3 nmol/L, reducing the cell viability by about 60%. Treatments 1-4 correspond to zinc nanoparticles at concentrations of 0.053 nmol/L, 0.106 nmol/L, 0.212 nmol/L, and 0.318 nmol/L, respectively. This reduction in viability compared well to that caused by 1 μmol/L staurosporine (treatment 5).

Figures 2E, 2F:
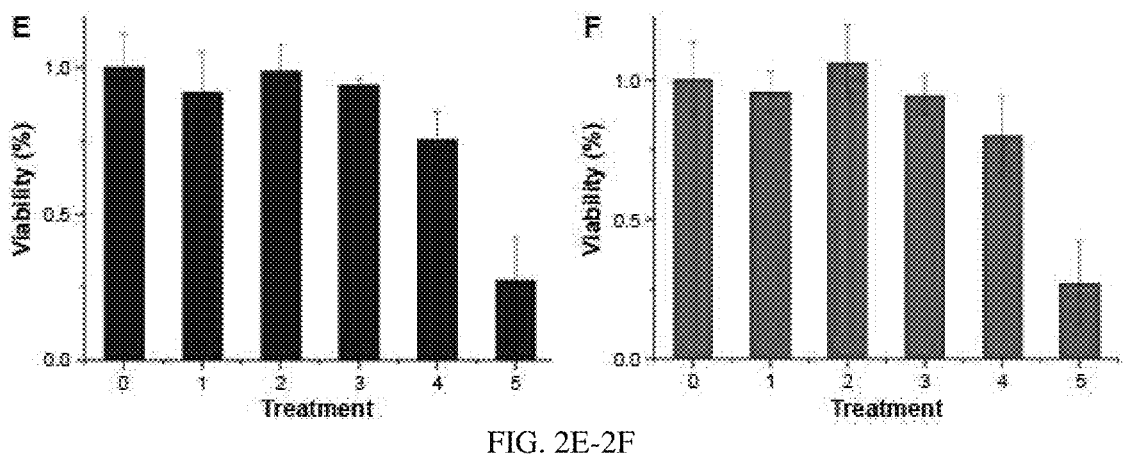
FIG. 2E shows viability of astrocytes at six experimental conditions related to treatment with zinc nanoparticles.
FIG. 2F shows viability of astrocytes at six experimental conditions related to treatment with copper nanoparticles.

As shown in FIG. 2E, noncancerous astrocytes were not affected, within the margin of error, by adding zinc nanoparticles at concentrations of 0.053 nmol/L, 0.106 nmol/L, 0.212 nmol/L, and 0.318 nmol/L (labeled treatments 1-4, respectively).

Similarly to the results with zinc, as shown in FIG. 2C, cell death due to treatment with copper nanoparticles was confirmed by MTT assay. The relative viability of RG2 glioma cells was reduced in a dose-dependent manner when added copper nanoparticle concentrations increased. Treatments 1-4 correspond to copper nanoparticles at concentrations of 0.017 nmol/L, 0.033 nmol/L, 0.066 nmol/L, and 0.1 nmol/L, respectively.

As shown in FIG. 2F, noncancerous astrocytes were not affected, within the margin of error, by adding copper nanoparticles at concentrations of 0.017 nmol/L, 0.033 nmol/L, 0.066 nmol/L, and 0.1 nmol/L (labeled treatments 1-4, respectively).

Without intending to be bound by theory, assuming that cell death is proportional to the number of bound metal nanoparticles, the ratio of relative number of dead (Y) and living (1−Y) cells can be determined according to the Hill equation. FIG. 2B shows a plot of Y/1−Y vs. the concentration zinc nanoparticles for glioma cell mortality. The values of $K_d$ and n obtained for zinc by viability experiments were 0.22±0.08 nmol/L (SE) and 1.45±0.17 (SE), respectively. $IC_{50}$ values for RG2 cells were 0.27±0.1 nmol/L (SE) for Zn. FIG. 2D shows a plot of Y/1−Y vs. the concentration of copper nanoparticles for glioma cell mortality. The values of $K_d$ and n obtained for copper nanoparticles were 0.12±0.02 nmol/L (SE) and 1.09±0.1 (SE), respectively. $IC_{50}$ values for RG2 cells were 0.26±0.1 nmol/L (SE) for Cu.

Figures 3A, 3B:
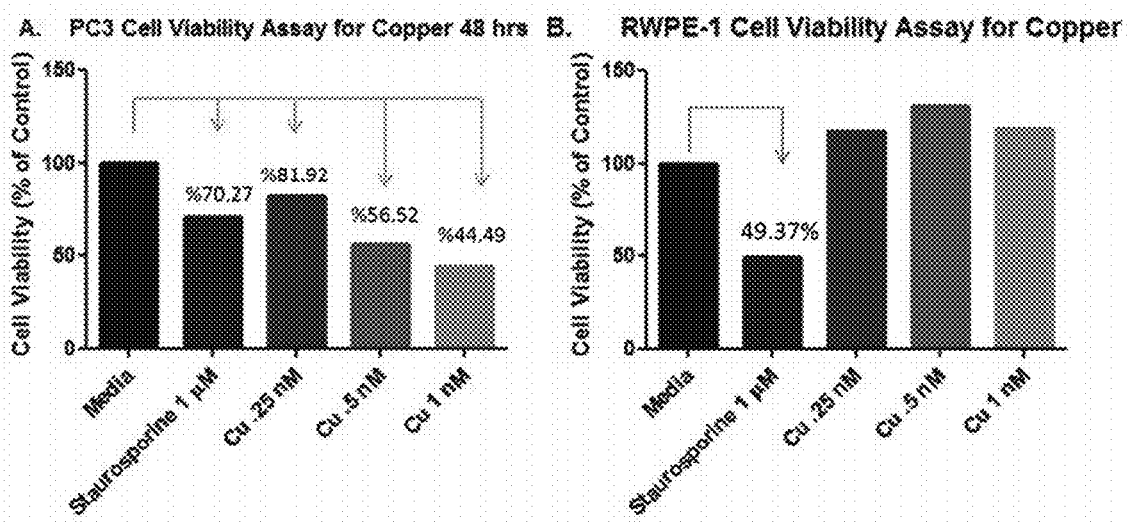
FIG. 3A shows viability of PC3 cells at five experimental conditions related to treatment with copper nanoparticles.
FIG. 3B shows viability of RWPE-1 cells at five experimental conditions related to treatment with copper nanoparticles.

Androgen dependent LNCaP, androgen independent PC3 cells, and normal prostate epithelium-derived RWPE-1 cells were also cultured with copper, zinc, silver, gold, or platinum nanoclusters. MTT cell proliferation assays showed a significant decrease in LNCaP and PC3 cell viability after treatment with copper or zinc compared to RWPE-1 cells, as shown in FIGS. 3A and 3B. Gold and platinum nanoparticles killed PC3 cells, but not LNCaP cells (androgen dependent) or RWPE-1 cells. Staurosporine, an apoptotic reagent, was used as a positive control. Cells were cultured for 48 hours. Data points are average of three experiments and eight replicas. The metal nanoparticles had estimated diameters of 1 nm-2 nm and were more than 85% non-oxidized.

Figures 4A, 4B, 4C:
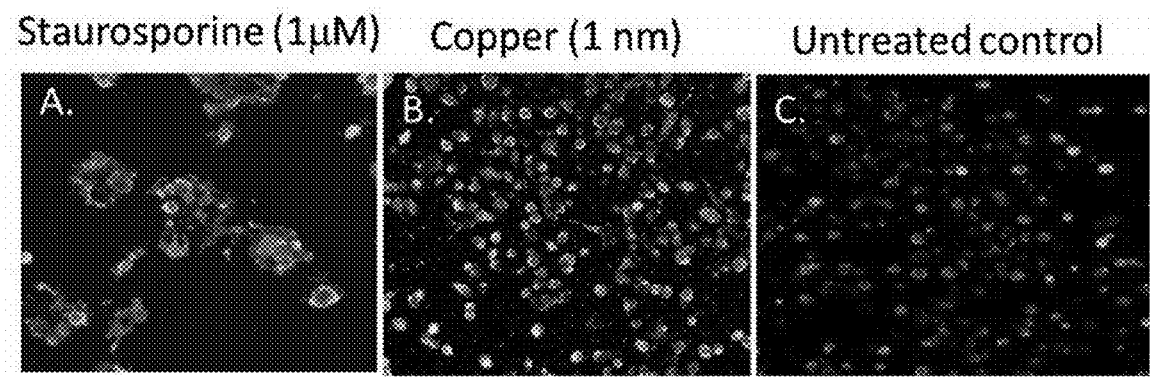
FIG. 4A shows fluorescent labeling of Annexin V in staurosporine-treated PC3 prostate cancer cells.
FIG. 4B shows fluorescent labeling of Annexin V in copper nanoparticle-treated PC3 prostate cancer cells.
FIG. 4C shows fluorescent labeling of Annexin V in untreated PC3 prostate cancer cells.

DNA fragmentation in PC3 cell samples of either untreated negative control, cells treated with 1 μM staurosporine, or cells treated with copper visually confirmed apoptosis, as shown in FIG. 4A-4C. Copper nanocluster-induced apoptosis was visually confirmed with Alexa 488-conjugated Annexin V, which binds apoptotic cells. As shown in FIG. 4B, increased fluorescent labeling of Annexin V in copper nanoparticles-treated PC3 prostate cancer cells suggests cell death by apoptosis. FIG. 4A shows a positive control with staurosporine and FIG. 4C shows a negative control.

Light Darkfield Images

Figures 5A, 5B:
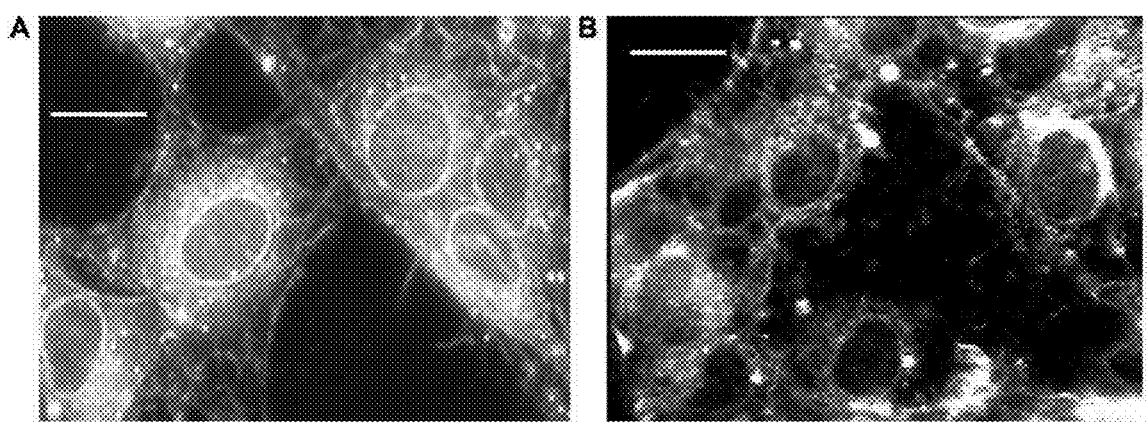
FIG. 5A shows a light darkfield image of RG2 glioma cells before exposure to zinc nanoparticles.
FIG. 5B shows a light darkfield image of RG2 glioma cells after exposure to 5 nmol/L of zinc nanoparticles.

Following incubation with zinc nanoparticles for 20 hours, cells displayed morphological features consistent with cell death, including a decrease in adherence, shrinking/rounding, nuclear condensation, and budding from cell bodies. FIG. 5A shows a light darkfield image of RG2 glioma cells before exposure to zinc nanoparticles. FIG. 5B shows a light darkfield image of the RG2 glioma cells after exposure to 5 nmol/L of zinc nanoparticles. Zn-induced cell injury was similar to the effects of 1 μmol/L staurosporine, an effective apoptotic reagent.

Example 4

PEGylation of Zinc Nanoparticles

Zinc nanoparticles of about 1.2 nm in size were prepared by a high-voltage electrical discharge method, as described in Example 1. Polyethylene glycol solutions of molecular weight 1000 g/mol or 400 g/mol (Sigma-Aldrich), PEG1000 or PEG400, respectively, were added to a suspension of the zinc nanoparticles to make 1% w/v of PEGs. Zinc nanoparticles PEGylated with 400 g/mol or 1000 g/mol molecular weight polyethylene glycol are referred to as ZnPEG400 and ZnPEG1000, respectively. The suspensions were heated to 40° C., purged with $N_2$ obtained from liquid nitrogen, and maintained at these conditions for 20 minutes. The suspensions were sonicated at 19 W and 40 kHz for 20 min.

Example 5

Properties of PEGylated Zinc Nanoparticles

Properties of the PEG coatings on the nanoparticle surface are shown in Table 1.

TABLE 1

Properties of PEG on the surface of zinc nanoparticles.

| Property | ZnPEG400 | ZnPEG1000 |
|---|---|---|
| Area per PEG single chain (nm$^2$) | 1.3 | 2.91 |
| Number of monomers in PEG | 9 | 23 |
| Thickness of PEG layer (nm) | 1.3 | 2.3 |

The PEGylated nanoparticles obtained according to Example 4 were characterized using transmission electron microscopy (TEM) and atomic force microscopy (AFM).

Figures 6A, 6B, 6C, 6D, 6E, 6F:
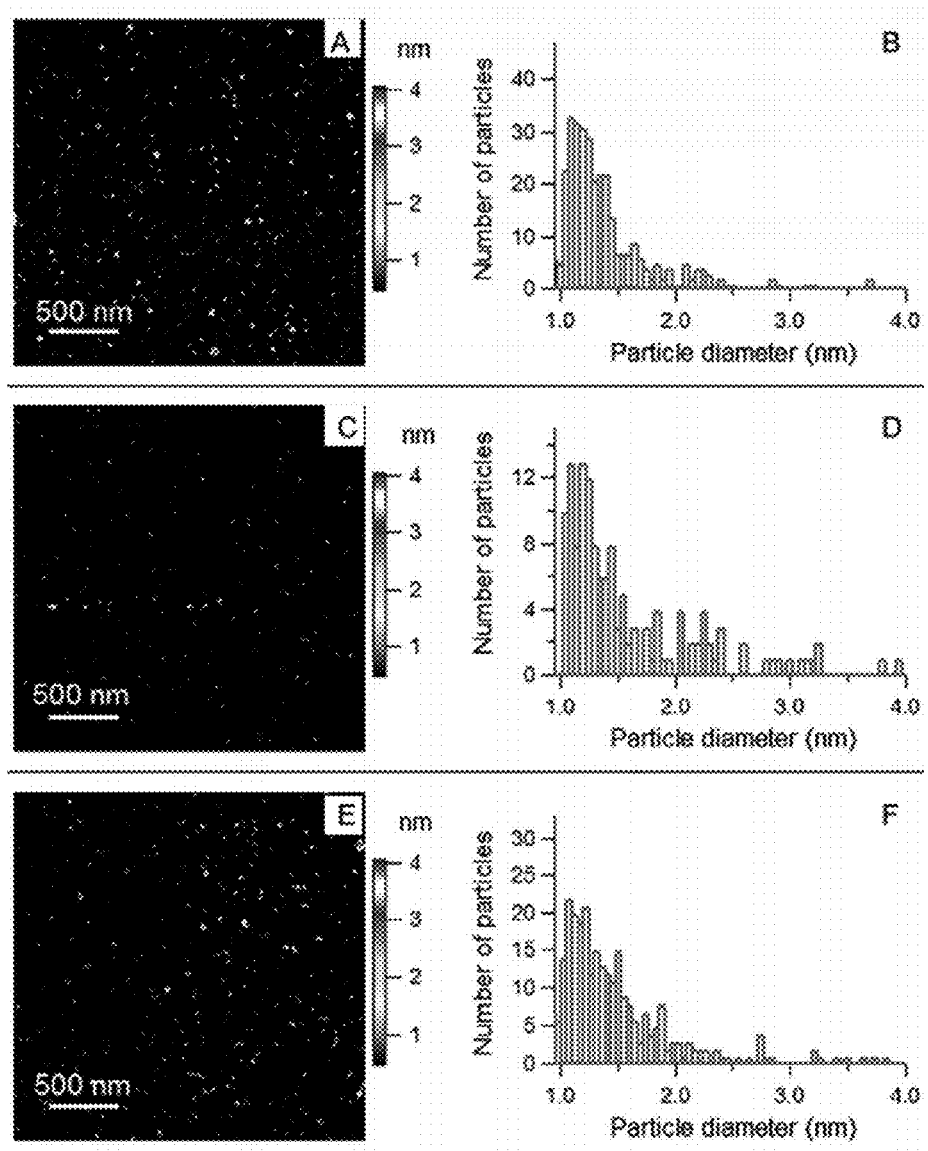
FIG. 6A shows an AFM image of uncoated zinc nanoparticles.
FIG. 6B shows a size distribution of the zinc nanoparticles of FIG. 6A.
FIG. 6C shows an AFM image of ZnPEG400 nanoparticles.
FIG. 6D shows a size distribution of the zinc nanoparticles of FIG. 6C.
FIG. 6E shows an AFM image of ZnPEG1000 nanoparticles.
FIG. 6F shows a size distribution of the zinc nanoparticles of FIG. 6E.

As shown in FIGS. 6A-6F, the physical properties of non-PEGylated zinc nanoparticles, ZnPEG400 nanoparticles, and ZnPEG1000 nanoparticles were compared using AFM. The diameter distribution of non-PEGylated zinc nanoparticles is shown in FIG. 6B. The non-PEGylated zinc nanoparticles had a mean size of 1.2±0.3 nm (SD). The diameter distributions of ZnPEG400 and ZnPEG1000 nanoparticles are shown in FIGS. 6D and 6F, respectively. The ZnPEG400 and ZnPEG1000 nanoparticles each had a mean size of 1.2±0.3 nm (SD).

Figures 7A, 7B, 7C, 7D, 7E, 7F:
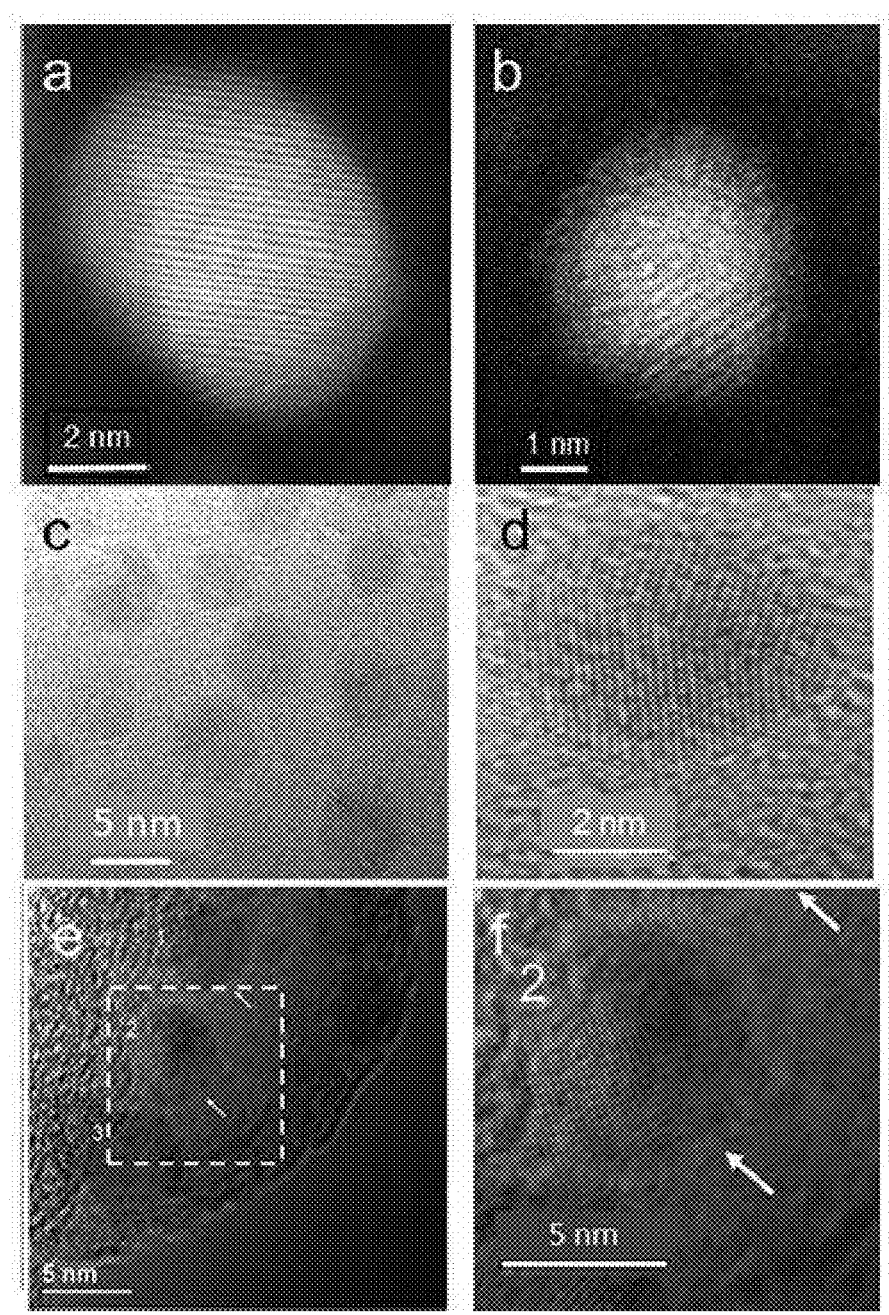
FIG. 7A shows a transmission electron microscope (TEM) image of non-PEGylated Zn nanoparticles at a first magnification.
FIG. 7B shows a TEM image of ZnPEG400 nanoparticles.
FIG. 7C shows a TEM image of the non-PEGylated Zn nanoparticles of FIG. 7A at a second magnification.
FIG. 7D shows a TEM image of the non-PEGylated Zn nanoparticles of FIG. 7A at a third magnification.
FIG. 7E shows a TEM image of ZnPEG1000 nanoparticles at a first magnification.
FIG. 7F shows a TEM image of the ZnPEG1000 nanoparticles of FIG. 7E at a second magnification.

As shown in FIGS. 7A-7F, TEM images were obtained for non-PEGylated zinc, ZnPEG400, and ZnPEG1000 nanoparticles. FIGS. 7A, 7C, and 7D show TEM micrographs of non-PEGylated Zn nanoparticles at different magnifications. FIG. 7B shows a TEM micrograph of ZnPEG400 showing the metal core and the PEG passivation layer. FIGS. 7E and 7F show TEM micrographs of ZnPEG1000 nanoparticles at different magnifications, where the labels 1, 2, 3 point to the nanoparticles with visible lattice fringe patterns, indicating their crystallinity. Arrows show layers surrounding nanoparticles that are presumed to be coatings of PEG1000. The characteristic fringes of 0.21 nm and 0.17 nm found in both non-PEGylated and PEGylated zinc nanoparticles match the (011) and (012) vectors for the hcp crystal lattice of zinc. Larger than average size particles are shown to emphasize the crystal fringes.

The crystalline structure of zinc nanoparticles revealed in this work is consistent with those obtained for zinc nanowires and nanorods. The extent of the similarities of the zinc lattices and core lattices of PEGylated zinc nanoparticles indicates that PEGylating maintains the crystalline nature of the metal particles.

Example 6

Time and Temperature Studies of PEGylated Zinc Nanoparticles

The PEGylated nanoparticles obtained according to Example 4 were also characterized using X-ray photoelectron spectroscopy (XPS). For the XPS experiments, the non-PEGylated and PEGylated zinc nanoparticles were subjected to four experimental conditions:
1. Particles were stored for 1 day at of 278 K (5° C.);
2. Particles were stored for 317 days at 278 K (5° C.);

3. Particles were stored for 2 days at the temperature of 303 K (30° C.); or

4. Particles were stored for 2 days at 323 K (50° C.).

Physical analyses of all samples were performed immediately after the end of each of the exposure conditions to minimize any changes in chemistry.

Figures 8A, 8B:
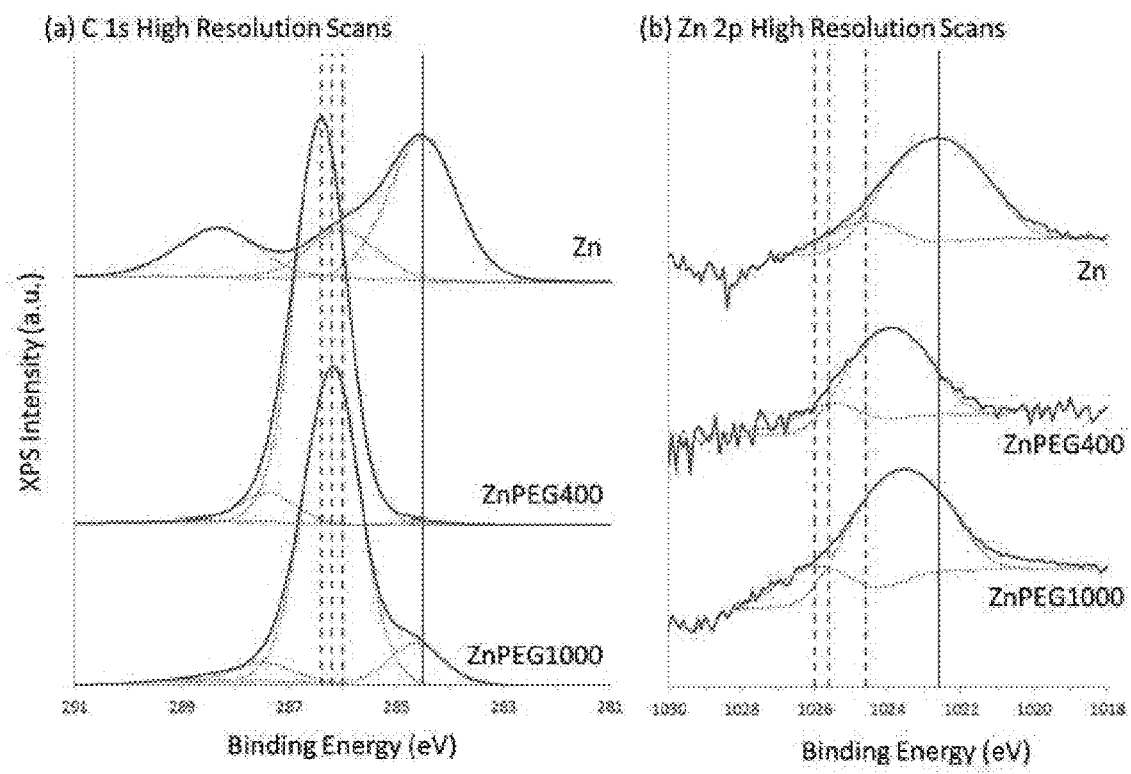
FIG. 8A show XPS spectra showing the C is core lines for uncoated zinc nanoparticles, ZnPEG400 nanoparticles, and ZnPEG1000 stored 1 day at 278 K (5° C.), with the spectra offset to facilitate viewing. The solid curves indicate the experimentally obtained spectra, with the dotted curves underneath indicating their best-fit chemical components.
FIG. 8B shows XPS spectra showing the Zn 2p3/2 core lines for the nanoparticles of FIG. 8A, shown in log scale and with the spectra offset to facilitate viewing. The solid curves indicate the experimentally obtained spectra, with the dotted curves underneath indicating their best-fit chemical components.

FIGS. 8A and 8B show representative XPS spectra obtained for freshly prepared non-PEGylated zinc and PEGylated zinc nanoparticles stored 1 day at 278 K (5° C.). For the C 1s spectra, the solid vertical line represents the position of the C—C peaks, to which all spectra were calibrated to, with the dotted lines showing the spectral shift of the C—O peaks, which were 286 eV, 286.4 eV, and 286.2 eV for the Zn, ZnPEG400, and ZnPEG1000 systems, respectively. Each spectrum represents an average of six spectral runs. For the Zn 2p plots, the solid line represents the position of the Zn peak for the bare Zn system, while the dotted lines show the spectral shift of the ZnO peaks, which were 1024.6 eV, 1025.6 eV, and 1026.0 eV for the Zn, ZnPEG400, and ZnPEG1000 systems, respectively. Each spectrum represents an average of six spectral runs.

A summary of the XPS data for non-PEGylated and PEGylated zinc nanoparticles for all four experimental conditions is shown in Table 2.

about 288.1 eV), zinc (Zn $2p_{3/2}$, about 1021.8 eV) and ZnO (Zn $2p_{3/2}$, about 1024 eV). The rise in the amplitude of C—O peak and the reduction in the binding energy of Zn $2p_{3/2}$ peaks in the ZnPEG400 and PEG1000 samples confirmed the successful PEGylation of zinc nanoparticles. The Zn $2p_{3/2}$ band showed that metallic zinc nanoparticles were oxidized only slightly.

The interaction of the PEG molecules and zinc nanoparticles affected the binding energies of carbon and zinc. Bonding of the PEG molecules onto the nanoparticles was associated with an increase in the binding energy of the C—O bond, and a corresponding decrease in the ZnO binding energy. The highest shift in binding energy was observed for ZnPEG400 nanoparticles stored at 278 K for 317 days. Similar shifts in binding energy were also observed for PEGylated zinc nanoparticles exposed to elevated temperatures of 303 K (30° C.) and 323 K (50° C.). These observations point to the covalent binding of PEG to the engineered zinc nanoparticles.

The XPS spectra of ZnPEG400 subjected to elevated temperature showed similar features to the nanoparticles stored for longer times. Without intending to be bound by theory, this observation provides evidence for the large number of covalently bound species and production of a conjugated electron system of zinc nanoparticles and PEG400 molecules.

TABLE 2

XPS properties of uncoated and PEGylated zinc nanoparticles, stored at various durations and temperatures.

| Sample | T (K) | Time (days) | Survey | | | High Resolution Zn 2p | | | |
|---|---|---|---|---|---|---|---|---|---|
| | | | O 1s (%) | C 1s (%) | Zn2p (%) | BE (eV) | Zn (%) | BE (eV) | ZnO (%) |
| Zn | 278 | 1 | 27.8 ± 2.3 | 70.5 ± 1.7 | 1.8 ± 0.1 | 1021.8 | 97.0 ± 0.8 | 1024.6 | 3.0 ± 0.8 |
| ZnPEG400 | 278 | 1 | 32.3 ± 0.5 | 67.4 ± 0.7 | 0.3 ± 0.1 | 1022.0 | 89.5 ± 4.0 | 1023.8 | 10.5 ± 4.0 |
| ZnPEG1000 | 278 | 1 | 30.3 ± 0.9 | 69.6 ± 2.1 | 0.1 ± 0.0 | 1021.9 | 88.0 ± 3.8 | 1023.5 | 12.0 ± 3.8 |
| Zn | 278 | 317 | 38.4 ± 1.0 | 60.2 ± 1.5 | 1.4 ± 0.1 | 1021.9 | 96.0 ± 1.0 | 1023.7 | 4.0 ± 1.0 |
| ZnPEG400 | 278 | 317 | 31.5 ± 0.1 | 68.4 ± 0.1 | 0.1 ± 0.0 | 1022.2 | 75.9 ± 8.2 | 1023.9 | 24.1 ± 8.2 |
| ZnPEG1000 | 278 | 317 | 31.1 ± 0.3 | 68.0 ± 0.4 | 0.9 ± 0.2 | 1021.9 | 86.1 ± 0.5 | 1024.2 | 13.9 ± 0.5 |
| Zn | 303 | 2 | 24.5 ± 4.1 | 75.1 ± 0.6 | 0.4 ± 0.1 | 1021.7 | 92.2 ± 3.5 | 1024.1 | 7.8 ± 3.5 |
| ZnPEG400 | 303 | 2 | 23.2 ± 4.4 | 76.6 ± 3.0 | 0.2 ± 0.0 | 1022.0 | 93.0 ± 2.8 | 1023.7 | 7.0 ± 2.8 |
| ZnPEG1000 | 303 | 2 | 24.6 ± 5.4 | 75.2 ± 5.2 | 0.2 ± 0.1 | 1021.8 | 94.2 ± 5.6 | 1023.4 | 5.8 ± 5.6 |
| Zn | 323 | 2 | 38.3 ± 5.3 | 60.8 ± 3.5 | 0.9 ± 0.3 | 1021.0 | 92.9 ± 3.3 | 1023.3 | 7.1 ± 3.3 |
| ZnPEG400 | 323 | 2 | 27.7 ± 4.6 | 72.1 ± 6.8 | 0.2 ± 0.1 | 1021.9 | 88.6 ± 2.6 | 1023.7 | 11.4 ± 2.6 |
| ZnPEG1000 | 323 | 2 | 21.8 ± 3.5 | 77.9 ± 2.7 | 0.3 ± 0.1 | 1021.7 | 92.7 ± 1.6 | 1024.0 | 7.3 ± 1.6 |

| Sample | T (K) | Time (days) | High Resolution C 1s | | | | | |
|---|---|---|---|---|---|---|---|---|
| | | | BE (eV) | C—C (%) | BE (eV) | C—O (%) | BE (eV) | C=O(OH) (%) |
| Zn | 278 | 1 | 284.3 | 66.2 ± 2.9 | 286.2 | 22.6 ± 1.5 | 288.5 | 11.2 ± 1.7 |
| ZnPEG400 | 278 | 1 | 285.0 | 3.7 ± 2.1 | 286.9 | 92.0 ± 3.0 | 288.5 | 4.3 ± 1.0 |
| ZnPEG1000 | 278 | 1 | 283.2 | 3.0 ± 0.6 | 286.7 | 94.5 ± 0.6 | 290.2 | 2.6 ± 0.0 |
| Zn | 278 | 317 | 284.4 | 60.2 ± 0.9 | 285.8 | 18.6 ± 0.7 | 288.1 | 21.2 ± 0.5 |
| ZnPEG400 | 278 | 317 | 285.0 | 0.9 ± 0.2 | 287.0 | 92.8 ± 0.9 | 288.0 | 6.3 ± 0.8 |
| ZnPEG1000 | 278 | 317 | 285.1 | 11.5 ± 2.4 | 286.7 | 83.5 ± 1.9 | 288.0 | 5.0 ± 0.8 |
| Zn | 303 | 2 | 284.4 | 60.8 ± 6.8 | 286.5 | 31.5 ± 4.0 | 289.2 | 7.7 ± 4.0 |
| ZnPEG400 | 303 | 2 | 284.4 | 38.9 ± 15.0 | 286.8 | 56.9 ± 15.3 | 288.8 | 4.2 ± 0.5 |
| ZnPEG1000 | 303 | 2 | 284.4 | 39.2 ± 14.9 | 286.6 | 55.7 ± 14.9 | 288.6 | 5.1 ± 1.1 |
| Zn | 323 | 2 | 284.2 | 65.6 ± 14.7 | 285.9 | 20.6 ± 8.8 | 288.2 | 13.8 ± 6.1 |
| ZnPEG400 | 323 | 2 | 284.4 | 35.2 ± 10.7 | 286.9 | 62.6 ± 12.7 | 283.7 | 2.2 ± 0.1 |
| ZnPEG1000 | 323 | 2 | 284.4 | 50.5 ± 15.7 | 286.5 | 43.7 ± 15.4 | 288.6 | 5.8 ± 0.8 |

The spectra were calibrated using the adventitious carbon C 1s peak at a binding energy of 284.6 eV, which allowed the identification of the following chemical species at their respective binding energies: hydrocarbon (C—C, about 285 eV), ether (C—O, about 286.1 eV), carboxyl (C=O(OH), Using an apparent concentration of primarily-elemental zinc as a function of time and storage temperature, the Arrhenius activation energies of oxidation were estimated by equation as shown in Table 3. After PEGylation, zinc nanoparticles showed reduction of the activation energy.

TABLE 3

Thermodynamic analysis of oxidation of Zn,
ZnPEG400, and ZnPEG1000 nanoparticles.

| Particle | T (° C.) | Estimated activation energy (kJ/mol) |
|---|---|---|
| Zn, 1.2 nm | 5-50 | 113 |
| Zn foil, 0.126 mm | 300-400 | 119 |
| ZnO powder, oxygen desorption | 86-97 | 96 |
| Molten Zn | 600-700 | 104 |
| ZnPEG400, 1.4 nm | 5-50 | 15.5 |
| ZnPEG1000, 1.4 nm | 5-50 | 34.9 |
| Pd/Fe nanoparticles, 60-100 nm | 20-35 | 39.47 |
| Pd/FePEG200 | 20-35 | 38.66 |

The change in the physical properties of zinc nanoparticles after PEGylation was also confirmed by determining zeta potential. The PEG binding resulted in a sharp reduction of zeta potential in water. Zeta potential was −42.4±4.8 (SE) mV, −26.1±2.5 (SE) mV (t(7)=7.96, p=0.0001), and −27.5±2.5 (SE) mV (t(7)=7.28, p=0.0001) for Zn, ZnPEG400, and ZnPEG1000 nanoparticles, respectively.

Example 7

Olfactory Studies of PEGylated Zinc Nanoparticles

To characterize the olfactory response properties of zinc nanoparticles under varying conditions, two sets of experimental settings were utilized:

(1) Non-PEGylated and PEGylated zinc nanoparticles were stored at 283 K (5° C.) and then employed, along with a standard odorant mixture in electroolfactogram (EOG) olfactory experiments over a storage period of 317 days; or (2) Non-PEGylated and PEGylated zinc nanoparticles were subjected to accelerated aging at temperatures of 303 K (30° C.) and 323 K (50° C.) for 2 days before the EOG experiments that followed directly after storage.

Non-PEGylated and PEGylated zinc nanoparticles mixed with eugenol, ethyl butyrate, or (±) carvone after storage and/or heating and odorant responses were tested by EOG with isolated rat olfactory epithelium (OE). An odorant mixture of 1.6 mmol/L each of ethyl butyrate, eugenol, and (+) and (±) carvone in water was prepared with a vortex mixer and stored in a dark glass container at 283K (5° C.). Odorants were obtained from Sigma-Aldrich.

The EOG instrumentation included Axon Instrument MultiClamp 700A amplifier and 1322A DigiData acquisition system. Rat OE was dissected out and positioned in a perfusion chamber such that the basal parts were immersed in physiological solution, while the olfactory cilia ware positioned in the water/air interface. Adult male Sprague±Dawley rats (Envigo, Dublin, Va.) weighing about 300 g were used. All olfactory experiments were performed ex vivo. Glass electrodes of about 24 μm tip openings were linked to the amplifier to record signals from the OE.

After the connection between the electrode and the OE was made, an air pulse of the odorant mixture was applied and a continuous EOG signal was recorded as function of time. A 0.25 s pulse of the odorant mixture at 55158 N/m² (8 psi) was generated by a computer-controlled Pneumatic PicoPump PV800 (World Precision Instruments, Sarasota, Fla.). A pulse of positive pressure pushed the odorant into a glass nozzle toward the OE. The computer controlled odorant delivery was comprised of 0.25 s pulses at 20 s and 60 s times for EOG data collection. The single EOG recording took 200 s and contained 10 response traces. A nanoparticle suspension was combined with odorant solutions to reach a final nanoparticle concentration of 0.02 nmol/L. During the pulse of delivery, the vapor of odorant with metal nanoparticles was transferred to the OE surface.

Figure 9:
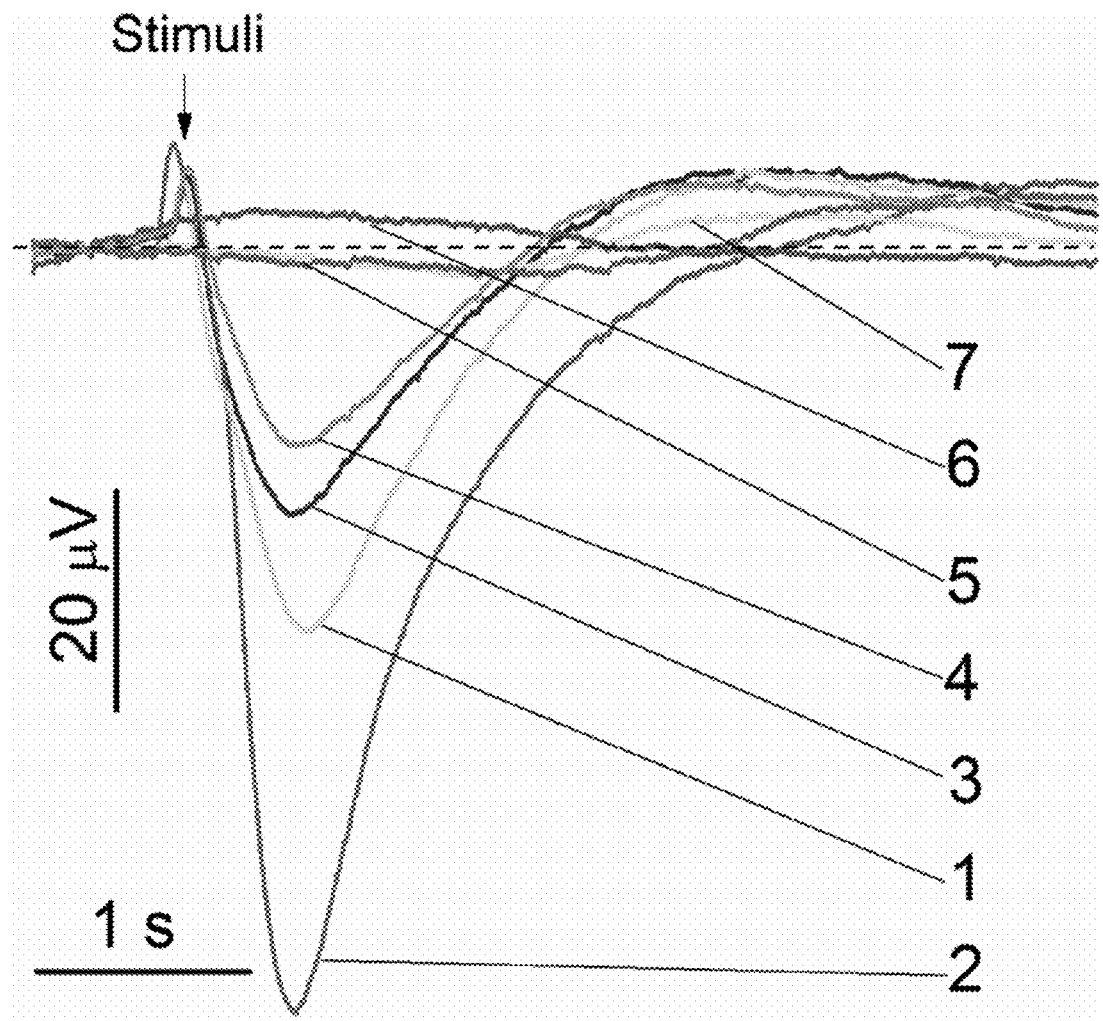
FIG. 9 shows electroolfactogram (EOG) recordings from rat olfactory epithelium produced by 0.25 s pulses of (1) odorant mixture, (2) odorant mixture+1.2 nm zinc nanoparticles, (3) odorant mixture+0.25 mmol/L PEG400, (4) odorant mixture+0.10 mmol/L PEG1000, (5) water vapor+PEG400, (6) water vapor+PEG1000, and (7) water vapor. The representative set of traces was obtained from 50 EOG traces.

Electroolfactograms are shown in FIG. 9. The EOG recordings from rat olfactory epithelium were produced by 0.25 s pulses of (1) odorant mixture, (2) odorant mixture+1.2 nm zinc nanoparticles, (3) odorant mixture+0.25 mmole/L PEG400, (4) odorant mixture+0.10 mmole/L PEG1000, (5) water vapor+PEG400, (6) water vapor+PEG1000, and (7) water vapor. The concentration of zinc nanoparticles and odorant mixture were 0.02 nmole/L and 1.6 mmole/L, respectively. The representative set of traces was obtained from 50 EOG traces.

The effects of PEG400 and PEG1000 without zinc nanoparticles were recorded from the rat OE, as depicted by traces 5 and 6. The EOG responses evoked by PEG400 and PEG1000 without the odorant mixture are small and nearly indistinguishable from the EOG signal of water, as depicted by trace 7. This result is consistent with polyethylene glycol being odorless. The EOG evoked by the odorant mixture with zinc nanoparticles (trace 2) showed a strong enhancement compared to the signal induced by the odorant mixture alone (trace 1). Combining odorants with ZnPEG400 and ZnPEG1000 resulted in the lower signals depicted by the traces 3 and 4, respectively.

The mean values of seven measurements of the relative responses to the odorant mixtures with Zn, ZnPEG400, and ZnPEG1000 were 2.69±0.11, 0.821±0.05, and 0.310±0.04, respectively. An analysis of variance showed that at the 0.05 level, the means were significantly different, $F(2, 18)=1900$, $p=0.000$.

The relative enhancement of olfactory responses by zinc nanoparticles was calculated as $(EOG_O+Zn-EOG_O)/EOG_O$, where $EOG_O$ was the peak of electrical response evoked by the odorant alone, and $EOG_O+Zn$ was the peak response stimulated by the mixture of the odorant and Zn nanoparticles. Similarly, the relative enhancements by ZnPEG400 and ZnPEG1000 were determined as $(EOG_O+ZnPEG400-EOG_O)/EOG_O$ and $(EOG_O+ZnPEG1000-EOG_O)/EOG_O$, respectively.

Figure 10:
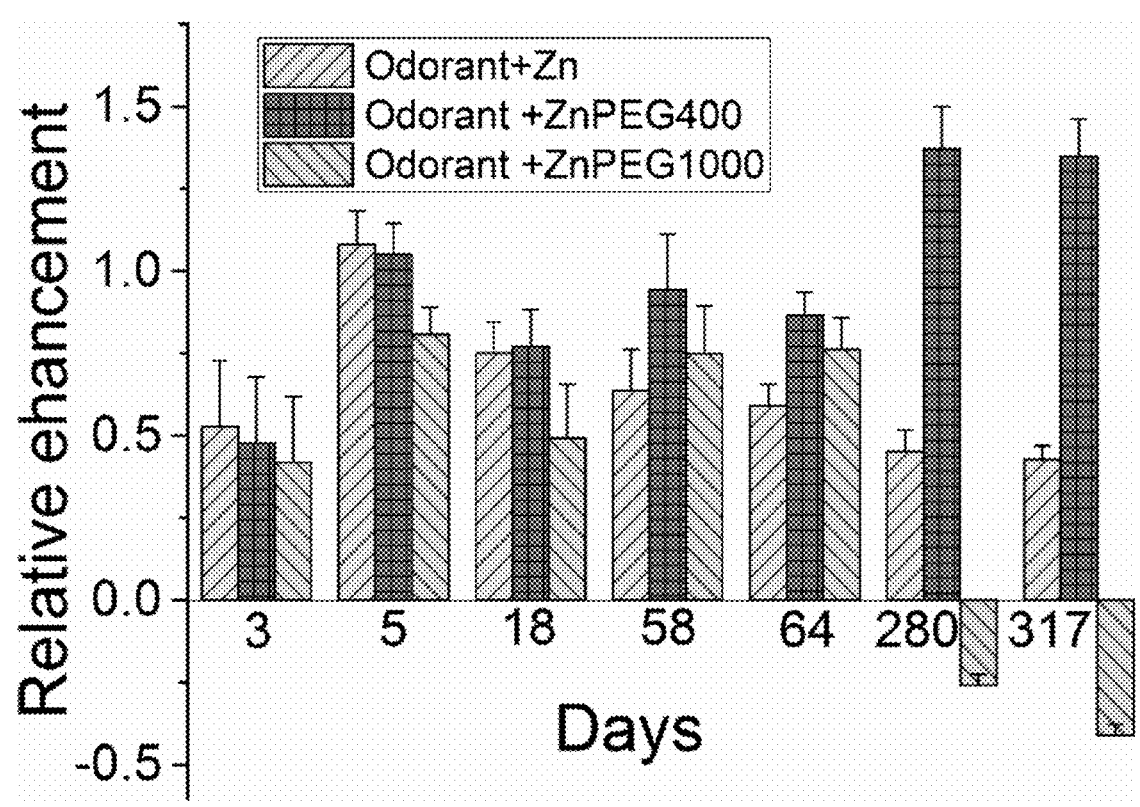
FIG. 10 is a chart showing the relative enhancement of EOG signals as a function of time of storage of zinc nanoparticles.

As shown in FIG. 10, the olfactory responses to odorant mixed with PEG400 or PEG1000 were tested systematically over the period of 317 days. The difference between peak values of EOG evoked by odorant and by non-PEGylated and PEGylated zinc nanoparticles was normalized by the EOG peak evoked by an odorant alone. As analysis of variance showed, at the level of 0.05, there was no significant difference between the relative olfactory responses to Zn, ZnPEG400, and ZnPEG1000 nanoparticles ranging from 3 days to 64 days of storage. After 280 days and 317 days of storage a significant difference between the relative olfactory responses to Zn, ZnPEG400, and ZnPEG1000 nanoparticles was observed.

Data indicate that stored ZnPEG400 nanoparticles maintain physiologically-consistent olfactory enhancement for over 300 days. Following 280 days of storage, ZnPEG400 provided the highest enhancement followed by Zn and then ZnPEG1000.

By these ex vivo experiments, enhancement was found to be dose-dependent, specific, and reversible. In conjunction with ex vivo analyses of sensory neurons in the rodent OE, in vivo cognitive effects on the brain regions associated with olfaction of non-anesthetized dogs were noninvasively analyzed using functional magnetic resonance imaging (fMRI). These studies indicated that engineered zinc nanoparticles added to odorant caused a significant rise of olfactory associated brain activity.

Figures 11A, 11B, 11C:
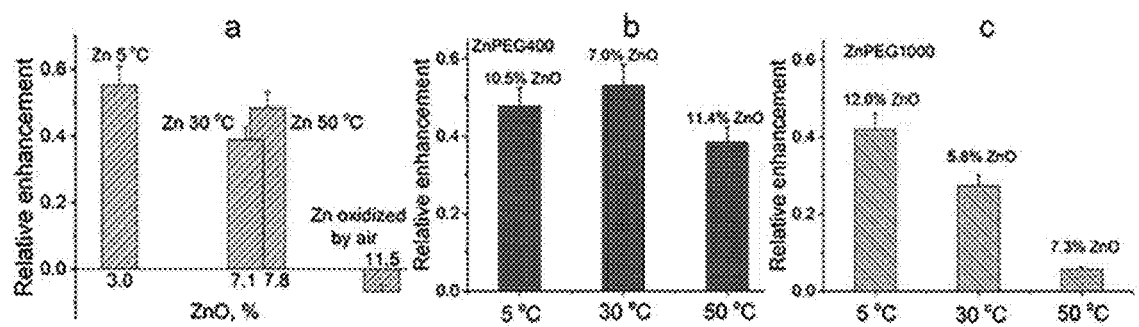
FIG. 11A is a chart showing the relative enhancement of EOG signals evoked by non-PEGylated zinc nanoparticles as a function of ZnO concentration.
FIG. 11B is a chart showing the relative enhancement of EOG signals evoked by ZnPEG400 nanoparticles as a function of ZnO concentration.
FIG. 11C is a chart showing the relative enhancement of EOG signals evoked by ZnPEG1000 nanoparticles as a function of ZnO concentration.

To further characterize effects of thermally-enhanced formation of ZnO on the odorant responses, the effects of non-PEGylated and PEGylated zinc nanoparticles stored for two days at an elevated temperature were analyzed. FIGS. 11A-11C show the relative enhancement of responses to odorants as the function ZnO concentration determined by XPS and temperature.

Referring to FIG. 11A, the difference between peak values of EOG evoked by odorant and by zinc nanoparticles was normalized by the EOG peak evoked by an odorant alone as a function of ZnO concentration that was determined by XPS. The first bar at 3% of ZnO, corresponds to zinc nanoparticles stored one day at 278 K (5° C.). The second and third bars reflect zinc nanoparticles stored for two days at 303 K (30° C.) and 323 K (50° C.), at 7.1% and 7.8% respectively. The forth bar at 11.5% of ZnO corresponds to the negative enhancement (inhibition) that was observed with zinc nanoparticles oxidized by percolating air.

Referring to FIG. 11B, the relative EOG enhancement produced by ZnPEG400 nanoparticles after they were stored for one day at 278 K (5° C.), two days at 303 K (30° C.) and 323 K (50° C.), respectively, is shown.

Referring to FIG. 11B, the relative EOG enhancement produced by ZnPEG1000 nanoparticles after they were stored for one day at 278 K (5° C.), two days at 303 K (30° C.) and 323 K (50° C.), respectively, is shown.

The relative olfactory enhancement by the zinc nanoparticles declined from 55% to −7%, when the ZnO concentration increased from 3.0% to 11.5%, as shown in FIG. 11A. The enhancement with ZnPEG1000 declined with the temperature, as shown in FIG. 11C. The enhancement with ZnPEG400, shown in FIG. 11B was less sensitive to zinc oxidation and temperature. The addition of the ZnPEG400 nanoparticles to odorant at the end of 317 days of storage at 278 K (5° C.) resulted in the highest relative EOG enhancement that was larger than enhancement by the un-PEGylated zinc nanoparticles.

The olfactory enhancement of approximately 140% using ZnPEG400 after 317 days of storage was not an anticipated result based on the higher level of ZnO of 24.1% ZnO compared to 10.5% for the freshly prepared ZnPEG400, as shown in Table 2. Although no significant change in the C—O concentration was observed, the C—C concentration decreased from 3.7% to 0.9%. Without intending to be bound by theory, the increase in the observed level of ZnO in this case does not imply a high level of oxidized zinc atoms, but suggests that a conjugated electron system between the zinc nanoparticles and PEG400 molecules forms that may be contribute to the increase in olfactory response.

The invention claimed is:

1. A pharmaceutical composition comprising a metal zinc nanoparticle and a coating, wherein the metal zinc nanoparticle has an average diameter of about 0.5 nm to about 5 nm,
    wherein less than about 15% of the metal zinc nanoparticle is oxidized, and
    wherein the coating comprises polyethylene glycol, wherein the polyethylene glycol has a molecular weight of 400 g/mol and
    wherein the metal zinc nanoparticle is capable of providing improved olfactory enhancement after 280 days of storage.

2. The pharmaceutical composition of claim 1, wherein the metal zinc nanoparticle has an average diameter of about 1 nm to about 2.5 nm.

3. The pharmaceutical composition of claim 1, wherein the metal zinc nanoparticle comprises about 30 atoms to about 60 atoms.

4. The pharmaceutical composition of claim 1, further comprising an excipient.

5. The pharmaceutical composition of claim 1, wherein the metal zinc nanoparticle has a purity of at least 99 wt. %.

6. The pharmaceutical composition of claim 1, wherein the metal zinc nanoparticle is formed by an underwater high-voltage discharge method, wherein the underwater high-voltage discharge method comprises applying a voltage of about 10,000 volts to about 20,000 volts to metal electrodes and creating an electric discharge.

7. The pharmaceutical composition of claim 6, wherein the metal zinc nanoparticle isolated by centrifugation.

8. The pharmaceutical composition of claim 1, wherein the metal zinc nanoparticle is capable of providing improved olfactory enhancement after 317 days of storage.

9. The pharmaceutical composition of claim 1, wherein coating is covalently bonded to the metal zinc nanoparticle.

* * * * *